United States Patent
Saphire

(10) Patent No.: US 8,802,439 B2
(45) Date of Patent: Aug. 12, 2014

(54) METHODS FOR ENHANCING INFECTIVITY OF RETROVIRUSES

(76) Inventor: Andrew Saphire, Solana Beach, CA (US)

( * ) Notice: Subject to any disclaimer, the term of this patent is extended or adjusted under 35 U.S.C. 154(b) by 70 days.

(21) Appl. No.: 13/321,509

(22) PCT Filed: May 18, 2010

(86) PCT No.: PCT/US2010/001461
§ 371 (c)(1),
(2), (4) Date: Nov. 18, 2011

(87) PCT Pub. No.: WO2010/134975
PCT Pub. Date: Nov. 25, 2010

(65) Prior Publication Data
US 2012/0064604 A1   Mar. 15, 2012

Related U.S. Application Data

(60) Provisional application No. 61/216,536, filed on May 18, 2009.

(51) Int. Cl.
*C12N 15/00* (2006.01)
(52) U.S. Cl.
USPC ........................................ 435/455
(58) Field of Classification Search
None
See application file for complete search history.

(56) References Cited

U.S. PATENT DOCUMENTS

| 6,855,549 | B1 | 2/2005 | McCray, Jr. et al. | |
| 2012/0064604 | A1* | 3/2012 | Saphire | 435/239 |

OTHER PUBLICATIONS

Pelopenese et al Peptidylproline cis-trans-Isomerase Pin1 Interacts with Human T-Cell Leukemia Virus Type 1 Tax and Modulates Its Activation of NF-B Journal of Virology, vol. 83, No. 7, Jan. 21, 2009, pp. 3238-3248.

* cited by examiner

*Primary Examiner* — Michael Burkhart
(74) *Attorney, Agent, or Firm* — T D Foster; Thomas D. Foster; Bruce Hare

(57) ABSTRACT

The present invention provides methods for producing retroviruses or viral vectors with enhanced infectivity. The methods entail transfecting a retroviral vector into a packaging cell that has suppressed expression or inhibited enzymatic activity of a parvulin prolyl peptidyl isomerase (parvulin PPIase), and culturing the transfected packaging cell to allow production of viral particles. The invention also provides methods for enhancing efficiency of gene transfer with a recombinant retrovirus. These methods involve constructing a recombinant retroviral vector expressing a target gene, transfecting into a packaging cell that has suppressed expression or inhibited enzymatic activity of a parvulin prolyl peptidyl isomerase (parvulin PPIase), culturing the transfected packaging cell to allow production of recombinant retroviral particles, harvesting recombinant retroviral particles from supernatant of the cultured cell, and transducing the recombinant retroviral particles into a target cell. Kits for carrying out these methods are also provided in the invention.

27 Claims, 9 Drawing Sheets

METHODS FOR ENHANCING INFECTIVITY OF RETROVIRUSES

CROSS-REFERENCE TO RELATED APPLICATIONS

The subject patent application claims the benefit of priority to U.S. Provisional Patent Application No. 61/216,536 (filed May 18, 2009) and PCT Patent Application No. PCT/US2010/001461 (filed May 18, 2010). The full disclosure of the priority applications are incorporated herein by reference in their entirety and for all purposes.

STATEMENT REGARDING FEDERALLY SPONSORED RESEARCH OR DEVELOPMENT

This invention was made with government support under AI074653 awarded by the National Institutes of Health. The government has certain rights in the invention.

BACKGROUND OF THE INVENTION

Viruses are highly efficient at nucleic acid delivery to specific cell types, while often avoiding detection by the infected host immune system. These features make certain viruses attractive candidates as gene-delivery vehicles for use in gene therapies. Retroviral vectors are the most commonly used gene delivery vehicles. The retroviral genome becomes integrated into lost chromosomal DNA, ensuring its long-term persistence and stable transmission to all future progeny of the transduced cell and making retroviral vector suitable for permanent genetic modification. Up to 8 kilo bases of foreign gene sequence can be packaged in a retroviral vector particles, which is more than enough for most gene therapy applications. The ability of retroviral vector particles to cause no detectable harm while entering their target cells represents another therapeutically important property. Retroviral based vectors can be manufactured in large quantities, which allows their standardization and use in pharmaceutical preparations. Most of the commonly used retroviral vectors are of uncovered origin. These vectors require cell division in order to achieve genome integration and long-term gene expression.

Lentiviral vectors are a particular type of retrovirus vectors. They have also been used as agents for the direct delivery and sustained expression of a transgene. Lentiviral based vectors can efficiently transduce dividing and non-dividing cells in these tissues, and maintain long-term expression of the gene of interest.

There is a need in the art for means for more efficiently transfecting retroviral vectors or transducing recombinant retroviruses in gene transfer. The present invention addresses this and other needs.

SUMMARY OF THE INVENTION

In one aspect, the invention provides methods for producing a retrovirus with enhanced infectivity. The methods involve (a) transfecting a retroviral vector into a packaging cell that has suppressed expression or inhibited enzymatic activity of a parvulin prolyl peptidyl isomerase (parvulin PPIase), (b) culturing the transfected packaging cell to allow production of viral particles. The methods can further entail harvesting viral particles from supernatant of the cultured cell. Some of the methods employ a human or monkey producer cell, and the parvulin PPIase inhibited or suppressed in the cell is Pin1.

In some of the methods, the packaging cell is transfected with the vector in the presence of a compound that specifically suppresses expression or inhibits enzymatic activity of the parvulin PPIase. In some methods, the packaging cell has suppressed expression of the parvulin PPIase, e.g., by knocking out a gene encoding the parvulin PPIase in the packaging cell. In some other methods, suppressed expression of the parvulin PPIase in the packaging cell is achieved by an inhibitory nucleic acid targeting a gene encoding the parvulin PPIase, e.g., a shRNA or a siRNA. In some methods, the employed packaging cell has inhibited enzymatic activity of the parvulin PPIase. This can be achieved by, e.g., a mutation in a gene encoding the parvulin PPIase or a recombinantly expressed peptide inhibitor of parvulin PPIase in the produce cell. Alternatively, the inhibited enzymatic activity can be realized with an antagonist compound of parvulin PPIase. In some specific embodiments, the antagonist compound employed in the methods is PiB or Juglone.

In another aspect, the invention provides methods for enhancing efficiency of gene transfer with a recombinant retrovirus. These methods entail (a) constructing a recombinant retroviral vector expressing a target gene, (b) transfecting into a packaging cell that has suppressed expression or inhibited enzymatic activity of a parvulin prolyl peptidyl isomerase (parvulin PPIase), (c) culturing the transfected packaging cell to allow production of recombinant retroviral particles, (d) harvesting recombinant retroviral particles from supernatant of the cultured cell, and (d) transducing the recombinant retroviral particles into a target cell. Some of the methods employ a human or monkey packaging cell, and the parvulin PPIase inhibited or suppressed in the cell is Pin1. In some of these methods, the packaging cell is transfected with the vector in the presence of a compound that specifically suppresses expression or inhibits enzymatic activity of the parvulin PPIase. For example, the packaging cell can have suppressed expression of the parvulin PPIase. This can be accomplished by using a packaging cell in which the endogenous gene encoding the parvulin PPIase is knocked out. Suppressed expression of the parvulin PPIase can also be achieved by using an inhibitory nucleic acid (e.g., a shRNA or a siRNA) targeting a gene encoding the parvulin PPIase. Some other methods employ a packaging cell that has inhibited enzymatic activity of the parvulin PPIase. Inhibited enzymatic activity of the parvulin PPIase in the packaging cell can be due to a mutation generated in the endogenous gene encoding the parvulin PPIase. It can also be achieved with an organic antagonist compound (e.g., PiB or Juglone) or a peptide inhibitor disclosed herein.

In a related aspect, the invention provides pharmaceutical combinations or kits for producing a retrovirus with enhanced infectivity. The kits typically contain an inhibitor compound of a parvulin prolyl peptidyl isomerase (parvulin PPIase) and a cell line for producing a retrovirus (e.g., human 293T cells). The kits can further contain an instruction for culturing the cell line transfected with a retrovirus in the presence of the inhibiting compound. The inhibitor compound can suppress expression of the parvulin PPIase (e.g., siRNA) or inhibits its enzymatic activity (e.g., an organic compound such as PiB). In some related embodiments, instead of a producer cell line that is independent of the inhibitor compound, the kits can contain a cell line which has been engineered to knock-out or knock-down expression of the parvulin PPIase (e.g., Pin1). Some other kits are specifically designed for producing recombinant retroviruses with enhanced infectivity. These kits can optionally further include a retroviral cloning vector for cloning a target gene of interest, and for producing recombinant retroviruses which express the target gene and which have enhanced infectivity.

A further understanding of the nature and advantages of the present invention may be realized by reference to the remaining portions of the specification and claims.

Figure 1:
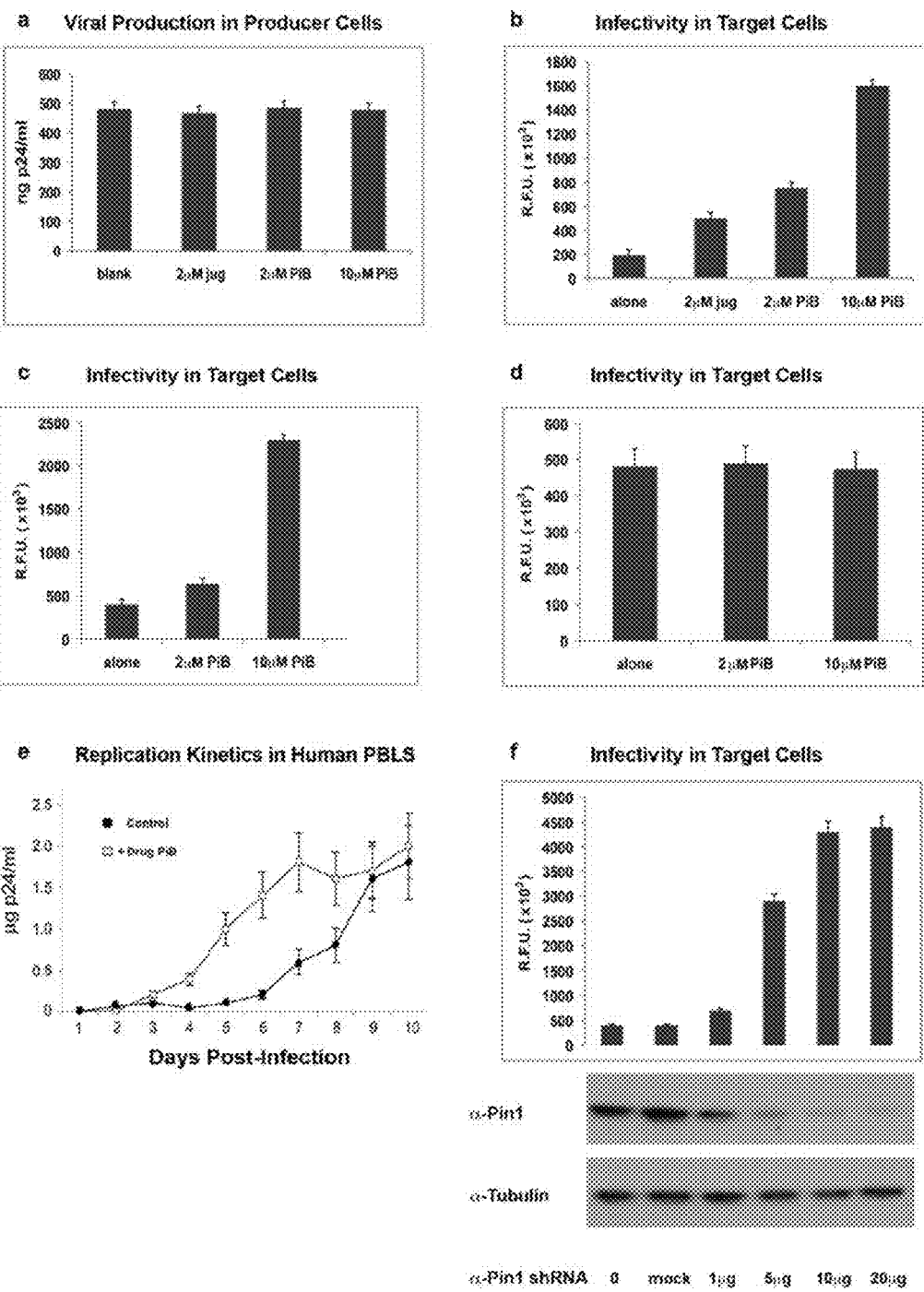
FIGS. 1A-1F show that down-regulation of Pin1 isomerase in producer cells enhances infectivity of HIV produced from the cells.

(A) Pin1 isomerase inhibitors do not alter viral production. 293T cells were transfected with a HIV-1 proviral construct (NL4.3) alone, or in the presence of 2.0 μM juglone, 2.0 μM PiB, or 10.0 μM PiB. Viral inocula were quantified by p24 enzyme-linked immunosorbent assay (PerkinElmer Life Sciences). Indicated on the y-axis are the concentrations of HIV-1 capsid (ng/ml) as measured by p24 ELISA, in the respective viral supernatants produced with 2.0 μM juglone or increasing concentrations of PiB (2.0 μM PiB, or 10.0 μM PiB) (x-axis) used to infect cells in FIG. 1b.

(B) Inhibition of Pin1 isomerase in producer cells enhances HIV-1 infectivity in a dose-dependent manner. Viral inocula from transfections above were normalized to equal virion particle number via p24 ELISA and used to infect target $CD4^+$ HeLa cells ($1 \times 10^5$ TZM-bl). Infectivity was scored using the Galacton-Star enzymatic galactosidase activity assay, and infectivity quantified by relative fluorescence units (R.F.U). We observed a 2 to 3-fold boost of infectivity with viruses produced in the presence of 2.0 μM Juglone or PiB, and a 8-fold boost with 10 μM PiB.

(C) Infectivity of VSV-G pseudotyped HIV-1 lacking gp160 is also enhanced by Pin1 isomerase inhibitors. 293T cells were co-transfected with a proviral construct encoding NL4.3 (Δenv) and a plasmid containing CMV-VSV-G, in the presence of 2 μM or 10 μM PiB. Viral supernatants were normalized by p24 and used to infect TZM-bl cells as above. Note that a smaller viral inoculum was used to account for the higher infectivity caused by VSV-G pseudotyping.

(D) Treatment of target cells with Pin1 isomerase inhibitors has no effect on HIV-1 infectivity. TZM-bl were pre-incubated with increasing concentrations of PiB (0, 2 μM, and 10 μM) for 24 hours prior to challenge with VSV-G pseudotyped virus. HIV-1 infectivity was measured 48 hours post-infection as above. Note that this is the same concentration of PiB and same duration of treatment that produces significant enhancement in producer cells.

(E) Replication kinetics of wild-type HIV-1 in human PBLs is enhanced by Pin1 isomerase inhibitors. $2 \times 10^6$ PBLs from patient donors were challenged with HIV-1 in the presence (lighter squares, top) or absence (black circles, bottom) of 10 μM PiB, which was added again at day 3 to maintain drug pressure. Replication was monitored by sampling virus concentration in supernatants via p24 ELISA.

(F) Genetic depletion of intracellular Pin1 levels in producer cells strongly enhances HIV-1 infectivity. 293T cells were transfected with 20 μg control pSilence vector, or increasing amounts of the Pin1-specific shRNA hPin1pSil (1 μg+19 μg control, 5 μg+15 μg control, 10 μg+10 μg control or 20 μg straight Pin1-specific shRNA). The Pin1-specific shRNA reduced the amount of endogenous Pin1 within 293T producer cells but did not alter the expression of α-tubulin. These cells were transfected with proviral NL4.3 and resultant viruses were normalized via p24 and used to infect TZMb1 cells as above. Each bar in the graph corresponds to the shRNA condition represented by the gel lane in blot below.

FIGS. 2A-2F show up-regulation of Pin1 in producer cells inhibits HIV infectivity.

(A) Over-expression of Pin1 in producer cells strongly inhibits HIV-1 infectivity. 293T cells were co-transfected with the NL4.3 proviral construct encoding HIV-1, CMV-VSV-G, and an expression vector encoding control pFLAG vector or human Pin1 (10 μg, 20 μg or 30 μg pFLAG-Pin1). Supernatants from these transfections were normalized by p24 ELISA and tested for infectivity on TZM-bl cells as described above. We see total knockdown of infectivity at 30 μg Pin1 in producer cells.

(B) Pin1 isomerase activity does not alter viral production. Concentrations of HIV-1 capsid in the viral supernatants used to infect cells in FIG. 2A, as measured by p24 ELISA, show that inhibiting Pin1 isomerase has little effect on viral production.

(C) Overexpressed Pin1 does not alter the relative ratios of gp120, reverse transcriptase, p17, or HIV-1 protease. Viruses were produced in the presence of increasing pFLAG-Pin1, isolated by sucrose gradient centrifugation, and probed for protein content via Western blot.

(D) Western blot of cell lysates with both anti-Pin1 and anti-FLAG show increased Pin1 expression relative to control actin. Note that the level of pFLAG-Pin1 expression is significantly higher than endogenous Pin1 expression.

(E) Loss-of-function Pin1 mutants fail to inhibit HIV-1. pFLAG-Pin1W34A and pFLAG-Pin1R68,69A, encoding WW-deficient and isomerase-defective Pin1, respectively, were individually co-transfected with the wild-type HIV-1 proviral and CMV-VSV-G. Supernatants were normalized via p24 ELISA and tested for infectivity as above.

(F) Inhibition by Pin1 correlates with its incorporation into HIV-1. Viruses were isolated by sucrose gradient centrifugation and probed for the presence of Pin1 by Western blot with rabbit anti-Pin1 (Santa Cruz). Over-expressed wild-type Pin1 is incorporated into HIV-1 in trans and inhibits HIV-1 infectivity in a dose-dependent manner whereas mutant Pin1 (R68, 69A or W34A) is not incorporated into virions and does not inhibit infectivity. Note the very high levels of pFLAG Pin1 incorporation compared to endogenous (HIV alone). Note also some proteolytic loss of the tag resulting in the doublet observed. Intervening lanes irrelevant to this experiment have been removed and left separate to make this obvious.

FIGS. 3A-3I show that Pin1 is a pan-retroviral inhibitor. 293T cells were transfected with HIV-1-GFP, SIV-GFP, bMLV-GFP, and nMLV-GFP proviral constructs, and in each case CMV-VSV-G, in the presence or absence of PiB or excess Pin1 as described above. Released virions were normalized via RT assay (EnzChek® Reverse Transcriptase Assay Kit), and infectivity on naïve TZMb1 cells was analyzed by GFP fluorescence via FACS (% cells infected).

(A) HIV-1 inhibited 7-fold by Pin1, boosted 3-fold by PiB.

(B) SIV inhibited 3-fold by Pin1, boosted 1.5-fold by PiB.

(C) bMLV inhibited 3.5-fold by Pin1, boosted 2-fold by PiB. The combined effect of modulating Pin1 had a 21-fold, 5.25-fold, and 7-fold effect on these retroviruses, respectively. Note also that these were obtained using a different means of quantifying virions and a different reporter system than previous experiments fully corroborate our prior findings.

(D) Inhibition of Pin1 prolyl isomerase activity does not enhance replication of the flavirius HCV. Cells persistently infected with HCV were treated with vehicle (DMSO), an MTP inhibitor (BMS-200150) capable of inhibiting HCV secretion, or with two doses of PiB (16 μM and 8 μM). After 1 hour of pre-treatment at 37° C., cells were washed with warm PBS and further incubated in normal medium containing the same drugs for an additional 9 hours at 37° C. Cell supernatants containing infectious HCV were collected for infectivity titer determination. These particles were assembled and secreted de novo during the time the cells were exposed to the drugs, as shown by the virtual absence of particles in cells treated with the HCV assembly inhibitor (BMS-200150). On the same day, we verified that this lot of PiB did effectively block HIV-1 in this HUH-7 cell line.

(E-G) Pin1 inhibition is target cell specific for bMLV and nMLV. (E) HIV-1, (F) bMLV, (G) nMLV were produced under conditions that inhibit or enhance Pin1 activity as above, normalized via RT activity, and identical supernatants were used to simultaneously infect TZMb1, OMK sMAGI, VERO, BSC1 and CV1 cells in duplicate. 48 hours later, total cellular GFP in target cells was measured via FACS. e) Infectivity of HIV-1 virions produced with drug was off scale at 59%. Boosts of bMLV in TZM cells and nMLV in OMK cells were slightly off scale.

(H) Blocking Pin1 isomerase activity rescues CypA-deficient HIV-1. Proviral constructs encoding wild-type NL4.3, or a CypA-deficient R9G89V mutant HIV-1 were used to transfect 293T cells, alone or in the presence of pFLAG-Pin1 or 10 μm PiB, normalized via p24 and used to infect TZMb1 cells and quantified as above. Not that despite the rather mild boost of wild-type virus in this particular experiment, the CypA-lacking virus is dramatically boosted. (H) and (I) Mutations in the HIV-1 capsid that permit HIV-1 to replicate in the absence of CypA confer resistance to Pin1 inhibition. At the same time as the experiment above, the proviral construct encoding the CypA-independent, CsA-dependent virus NL4.3A92E was used to transfect 293T cells, alone or in the presence of pFLAG-Pin1 or 10 μm PiB, normalized via p24 and used to infect TZMb1 cells and quantified as above. This mutant virus was entirely refractory to Pin1 modulation: neither significantly inhibited by Pin1 nor boosted by blocking Pin1 activity (I).

In a separate experiment, the proviral construct encoding the wild-type or the CypA-independent NL4.3CAi2 mutant were used to transfect 293T cells with or without co-transfected pFLAG-Pin1, normalized via p24 and used to infect TZMb1 cells as above. Note that this CypA-independent virus is also refractory to Pin1 inhibition. Also note that because the HIV-1 mutant NL4.3A92E is actually CsA dependent and replicates poorly in its absence, the target cells for this virus were incubated with 2 μm CsA, whereas no CsA was added to target cells infected with NL4.3CAi2.

Figure 4:
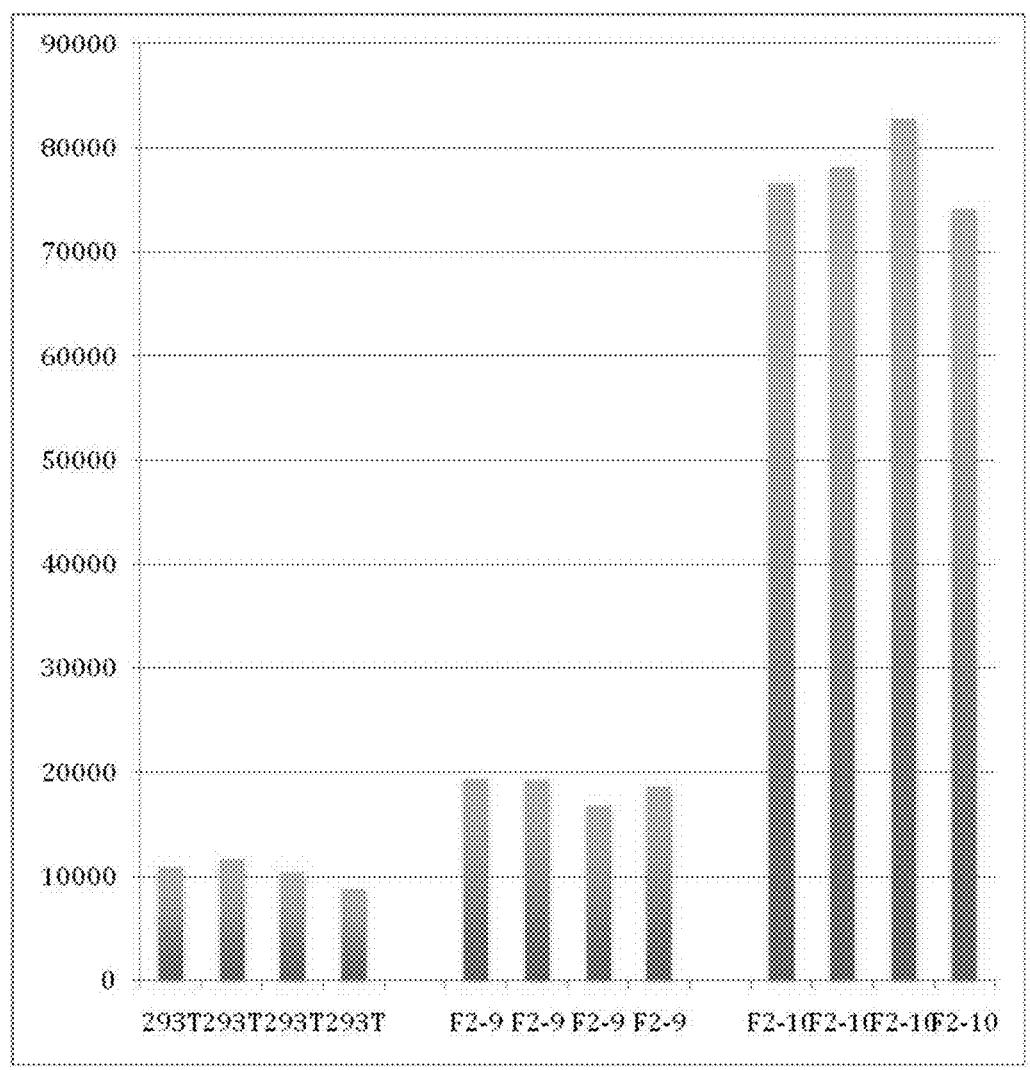

FIG. 4 shows that viruses produced in cells with stable Pin1 knocked-down are more infectious than those produced in wild type cells.

Figure 5:
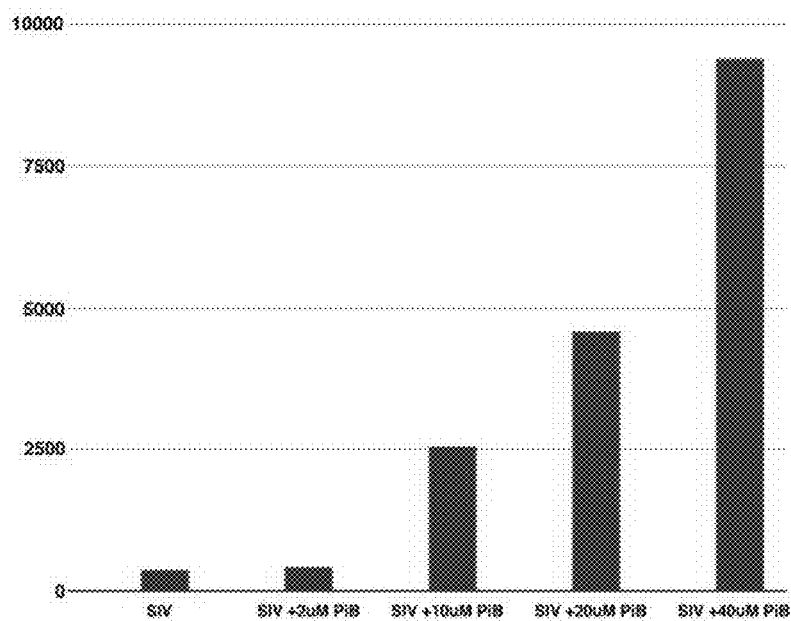

FIG. 5 shows enhanced infectivity of macaque SIV when produced from cells which have been treated with Pin1 inhibitors.

Figure 6:
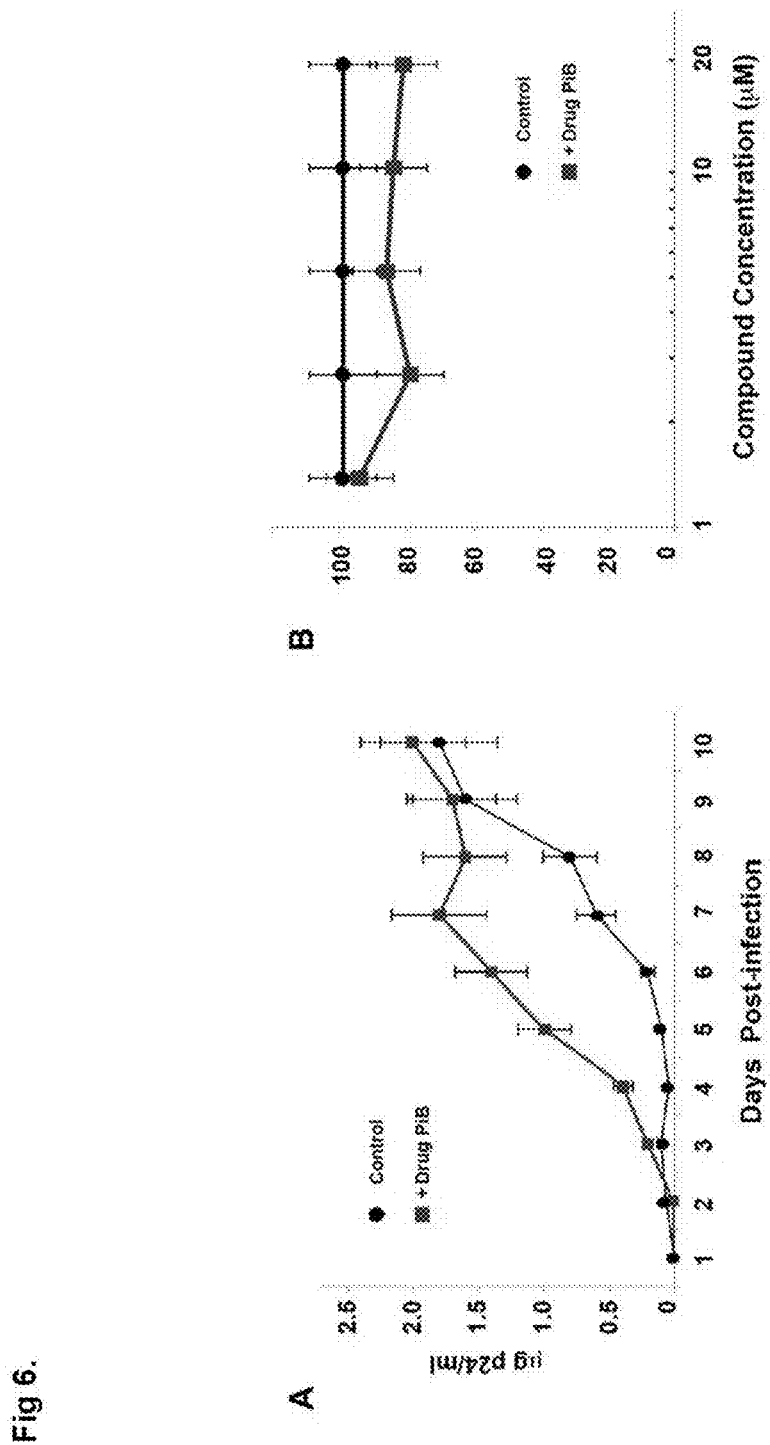

FIGS. 6A-6B show that Pin1 inhibitors can enhance replication kinetics of HIV-1 in human PBLs (B).

FIGS. 7A-7C show that HIV and MLV produced in cells with Pin1 blocking have enhanced infectivity in various primate cell lines.

FIG. 8 shows that blocking Pin1 activity in mouse embryonic fibroblast producer cells yields viruses with enhanced infectivity.

FIG. 9 shows that blocking Pin1 activity in non-human primate producer cells yields viruses with enhanced infectivity.

DETAILED DESCRIPTION OF THE INVENTION

I. Overview

The present invention is predicated in part on the discoveries by the present inventors that a prolyl isomerase, Pin1, attenuates infectivity of retroviruses. Specifically, as detailed in the Examples below, it was found that inhibition of Pin1 isomerase in HIV-1 producer cells boosts virion infectivity, and that overexpression of Pin1 in producer cells inhibits HIV-1 infectivity. In addition, the inventors observed that Pin1 does not alter the relative ratio of key viral proteins, and that the isomerase activity of Pin1 is specifically responsible for HIV-1 inhibition. Also, it was found that Pin1 is a pan-retroviral inhibitor as other retroviruses such as SIV and bMLV all showed the same response to Pin1: excess Pin1 inhibits all of these viruses, and Pin1 inhibitors boost their infectivity. Enhanced infectivity was also observed with SIV produced in cells with Pin1 inhibition or HIV produced in cells with stable Pin1 knock-down. It was also found that Pin1 inhibition enhances HIV replication kinetics. The inventors additionally found that Pin1 blocking in producer cells enhances viral infectivity towards various target cells, and that the enhanced viral infectivity by blocking Pin1 can be realized with either human or non-human producer cells.

In accordance with these studies, the present invention provides methods for producing retroviruses with enhanced infectivity. The invention also provides methods for enhancing efficiency of gene transfer with recombinant retroviruses. In general, the methods of the invention involve inhibiting a parvulin PPIase (e.g., Pin1) in a producer cell in which the recombinant retroviruses or viral vectors are produced. The methods of the invention can be broadly applied to any gene targeting systems that are based on viral vectors derived from retroviruses, e.g., HIV-1, SIV, HIV2, N-tropic MLV (nMLV) or B-tropic MLV (bMLV). The methods can be used alone or in combination with other known methods to enhance transfection or transduction efficiency. Kits for carrying out the various methods disclosed herein are also provided in the invention.

With the methods and kits disclosed herein, the efficiency of any retro or lentiviral gene delivery system can be enhanced without any modification of the system itself (e.g., a retroviral vector used to transfer an exogenous gene into a target host or cell). The advantageous afforded by the present invention also include, e.g., low costs as many inhibitors of parvulin PPIases (e.g., Pin1) are already commercially available. Further, there are no additional health concerns in the practice of the invention. This is because inhibition of parvulin PPIase (e.g., with a specific inhibitor compound) only involves the producer cell for generating a recombinant retrovirus. It does not involve the target subject, cell or plant into which the recombinant retrovirus is to be transduced. In other words, the employed inhibitor compound is used only during the production of the gene delivery system (e.g., a recombinant retrovirus), not its administration to the target cell, plant or subject. Prior to the gene transfer, there is no need for any additional treatment or manipulation of the target cell or subject. Thus, there are no concerns with respect to toxicity in the target cell or host.

The following sections provide more detailed guidance for practicing the present invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic

*Chemistry*, Kumar and Anandand (Eds.), Anmol Publications Pvt. Ltd. (2002); and *A Dictionary of Biology (Oxford Paperback Reference)*, Martin and Hine (Eds.), Oxford University Press (4th ed., 2000). In addition, the following definitions are provided to assist the reader in the practice of the invention.

The term "analog" is used herein to refer to a molecule that structurally resembles a reference molecule but which has been modified in a targeted and controlled manner, by replacing a specific substituent of the reference molecule with an alternate substituent. Compared to the reference molecule, an analog can exhibit the same, similar, or improved utility. Methods for synthesizing and screening candidate analog compounds of a reference molecule to identify analogs having altered or improved traits (e.g., an analog inhibitor compound with enhanced inhibitory activity on an enzyme such as Pin1) are well known in the art.

The term "antagonize" refers to the ability of a compound (e.g., a small molecule compound) to inhibit, disrupt or perturb a specific reaction, interaction or binding between a target polypeptide (e.g., an enzyme such as Pin1) and a cognate partner (e.g., a substrate). The compound can exert its antagonist activity by inhibiting, suppressing or interfering with a biological or biochemical activity (e.g., an enzymatic activity) of the target polypeptide and/or the cognate partner. The compound can also exert its activity by preventing the target polypeptide and its cognate partner to bind to each other.

The term "contacting" has its normal meaning and refers to combining two or more agents (e.g., two compounds or a compound and a cell) or combining agents and cells. Contacting can occur in vitro, e.g., mixing a compound and a cultured cell in a test tube or other container. It can also occur in vivo, e.g., binding of a compound to another compound (e.g., a polypeptide or polynucleotide) within a cell.

Host cell restriction refers to resistance or defense of cells against viral infections. Mammalian cells can resist viral infections by a variety of mechanisms. Viruses must overcome host cell restrictions to successfully reproduce their genetic material.

A ligand is a molecule that is recognized by a particular antigen, receptor or target polypeptide. Examples of ligands that can be employed in the practice of the present invention include, but are not restricted to, agonists and antagonists for cell membrane receptors, enzyme substrates, small molecule binding compounds, and monoclonal antibodies.

Retroviruses are enveloped viruses that belong to the viral family Retroviridae. The virus itself stores its nucleic acid, in the form of a +mRNA (including the 5'-cap and 3'-PolyA inside the virion) genome and serves as a means of delivery of that genome into host cells it targets as an obligate parasite, and constitutes the infection. Once in a host's cell, the virus replicates by using a viral reverse transcriptase enzyme to transcribe its RNA into DNA. The DNA is then integrated into the host's genome by an integrase enzyme. The retroviral DNA replicates as part of the host genome, and is referred to as a provirus. Retroviruses include the genus of Alpharetrovirus (e.g., avian leukosis virus), the genus of Betaretrovirus; (e.g., mouse mammary tumor virus), the genus of Gammaretrovirus (e.g., murine leukemia virus or MLV), the genus of Deltaretrovirus (e.g., bovine leukemia virus and human T-lymphotropic virus), the genus of Epsilonretrovirus (e.g., Walleye dermal sarcoma virus), and the genus of Lentivirus.

Lentivirus is a genus of viruses of the Retroviridae family, characterized by a long incubation period. Lentiviruses can deliver a significant amount of genetic information into the DNA of the host cell, so they are one of the most efficient methods of a gene delivery vector. Examples of lentiviruses include human immunodeficiency viruses (HIV-1 and HIV-2), simian immunodeficiency virus (SIV), and feline immunodeficiency virus (FIV). Additional examples include BLV, EIAV and CEV.

The term "mutagenesis" or "mutagenizing" refers to a process of introducing changes (mutations) to the base pair sequence of a coding polynucleotide sequence and consequential changes to its encoded polypeptide (e.g., a parvulin PPIase). Unless otherwise noted, the term as used herein refers to mutations artificially introduced to the molecules as opposed to naturally occurring mutations caused by, e.g., copying errors during cell division or that occurring during processes such as meiosis or hypermutation. Mutagenesis can be achieved by a number of means, e.g., by exposure to ultraviolet or ionizing radiation, chemical mutagens, or viruses. It can also be realized by recombinant techniques such as site-specific mutagenesis, restriction digestion and relegation, error-prone PCR, polynucleotide shuffling and etc. For a given polynucleotide encoding a target polypeptide, mutagenesis can result in mutants or variants that contain various types of mutations, e.g., point mutations (e.g., silent mutations, missense mutations and nonsense mutations), insertions, or deletions.

The term "operably linked" when referring to a nucleic acid, means a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide is polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as nucleotide polymers.

Polypeptides are polymer chains comprised of amino acid residue monomers which are joined together through amide bonds (peptide bonds). The amino acids may be the L-optical isomer or the D-optical isomer. In general, polypeptides refer to long polymers of amino acid residues, e.g., those consisting of at least more than 10, 20, 50, 100, 200, 500, or more amino acid residue monomers. However, unless otherwise noted, the term polypeptide as used herein also encompass short peptides which typically contain two or more amino acid monomers, but usually not more than 10, 15, or 20 amino acid monomers.

Proteins are long polymers of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies. In some embodiments, the terms polypeptide and protein may be used interchangeably.

A cell has been "transformed" or "transfected" by exogenous or heterologous polynucleotide when such polynucleotide has been introduced inside the cell. The transforming polynucleotide may or may not be integrated (covalently linked) into the genome of the cell. In prokaryotes, yeast, and mammalian cells for example, the transforming polynucleotide may be maintained on an episomal element such as a plasmid. With respect to eukaryotic cells, a stably transformed cell is one in which the transforming polynucleotide has become integrated into a chromosome so that it is inherited by daughter cells through chromosome replication. This stability is demonstrated by the ability of the eukaryotic cell to establish cell lines or clones comprised of a population of daughter cells containing the transforming polynucleotide. A "clone" is a population of cells derived from a single cell or common ancestor by mitosis. A "cell line" is a clone of a primary cell that is capable of stable growth in vitro for many generations.

A "variant" of a target polypeptide refers to a molecule which has a structure that is derived from or similar to that of the target polypeptide. Typically, the variant is obtained by mutagenesis of the target polypeptide in a controlled or random manner. As detailed herein, methods for performing mutagenesis of a polypeptide are well known in the art, e.g., site-specific mutagenesis, error-prone PCR, restriction digestion and relegation, and polynucleotide shuffling.

A "vector" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

A retrovirus (e.g., a lentivirus) based vector or a vector derived from the virus means that genome of the vector comprises components from the virus as a backbone. The viral particle generated from the vector as a whole contains essential vector components compatible with the RNA genome, including reverse transcription and integration systems. Usually these will include the gag and pol proteins derived from the virus. If the vector is derived from a lentivirus, the viral particles are capable of infecting and transducing non-dividing cells. Recombinant retroviral particles are able to deliver a selected exogenous gene or polynucleotide sequence such as therapeutically active genes, to the genome of a target cell.

III. Parvulin Prolyl Isomerases Inhibit Retroviruses by Enhancing Host Cell Restriction The invention provides methods of enhancing infectivity of retroviruses and retroviral vectors by inhibiting activities of parvulin peptidyl-prolyl isomerases. These methods are based on the discovery by the present inventors of broad anti-retroviral activity of parvulin peptidyl-prolyl isomerases. Peptidyl-prolyl isomerases (PPIases) are enzymes found in both prokaryotes and eukaryotes that interconvert the cis and trans isomers of peptide bonds with the amino acid proline. The parvulin peptidyl-prolyl isomerases belong to a family of PPIases that include the human parvulin peptidyl-prolyl isomerase (Pin1), *Escherichia coli* enzyme parvulin, yeast enzyme ESS1, *Drosophila* enzyme dodo, and *Arabidopsis thaliana* enzyme Pin1 (see, e.g., Chao et al., Nuc. Acids. Res. 29:767-73, 2001). All eukaryotic parvulin PPIase family members have in common the presence of a WW domain that is involved in the recognition and association of the conserved motifs, phosphoserine-proline and phosphothreonine-proline, and a PPIase domain that contains its enzymatic activity.

As described in detail in the Examples below, Pin1 exerts real-time attenuation of wild-type HIV-1 replication, as evidenced by the fact that physiological levels of human Pin1 attenuate wild-type HIV-1 replication, and that pharmacologic or genetic knock-down of Pin1 in human cells boosts HIV-1 replication. It was also found that viral susceptibility to Pin1 inhibition maps to the HIV-1 capsid protein, and that HIV-1 capsid mutants which replicate independently of cyclophilin A are resistant to Pin1 inhibition. In addition, it is specifically the prolyl isomerase activity of Pin1 that is responsible for inhibition. Further, Pin1 also inhibits other retroviruses such as SIV, nMLV and bMLV. Interestingly, Pin1 functions in the producer cell, as virions isolated from producer cells with elevated Pin1 activity are significantly less infectious than virions derived from wild-type cells. More over, it was also observed that Pin1 has no effect on production, maturation or assembly of retroviruses.

The findings disclosed herein are important because they suggest that HIV-1 and the other retroviruses (especially lentiviruses) have not evolved fully effective countermeasures against Pin1. By comparison, blocking other human factors such as ABOBEC3G or human TRIM5α has no effect on wild-type HIV-1 (Vif+) infectivity in human cells. Like APOBEC3G, Pin1 appears to act in the producer cell in a manner that is only manifested after entry into target cells. While Pin1 can associate with APOBEC3G, it is unlikely that APOBEC3G or Vif are targets of Pin1 inhibition. This is because (1) the producer cells in which Pin1 mediated HIV-1 inhibition was observed lack APOBEC3G, and 2) the target HeLa cells used are fully permissive to HIV-1 lacking Vif.

As demonstrated in the Examples, the antiviral activity of Pin1 is dependent on its prolyl isomerase activity. In addition, mutations in the CypA-binding loop of the HIV-1 capsid lower susceptibility to Pin1, suggesting a possible mechanism for Pin1 inhibition. Not wishing to be bound by any theory, it is possible that Pin1 isomerizes this locus so that the retroviral capsid is better recognized by restriction factors. Based on NMR studies, the G89-P90 couplet in HIV-1 CA is approximately 86% in the trans and 14% in the cis state (Bosco et al., Proc. Natl. Acad. Sci. USA 99:5247-52, 2002). Intriguingly, in most proteins analyzed, Pin1 isomerization favors equilibrium of the cis conformation. Elevated Pin1 activity may enhance restriction by increasing the relative ratio of cis to trans G89-P90 within the capsid. By contrast, CypA may oppose a conformational equilibrium dictated by Pin1, suggesting at least one reason why host CypA is specifically recruited by HIV-1. However, since Pin1 binds preferentially to phosphorylated serine-proline sites, it is possible that Pin1 binds to a different site on capsid, separate from the CypA-binding site. Three sites in which phosphorylated serines abut prolines occur in the HIV-1 capsid, and similar sites occur in the capsids of the other retroviruses tested here. One or all of these phosphorylated Ser-Pro sites may represent the Pin1 target.

A further consequence of the proline-isomerization mechanism may explain the plurality of retroviruses inhibited by Pin1. It has been shown that both sequence and structure are determinants of host cell restriction (Xu et al., Genes Dev.

17:2765-76, 2003). Since Pin1 alters structure, rather than sequence, this may explain why Pin1 can heighten restriction against multiple retroviruses. In each instance, the only commonality may be the requirement for the proline to be in conformation best recognized by the restriction factor, regardless of the identity of the particular factor. This may explain why Pin1 enhances restriction, but does not alter restriction specificity.

The finding of an inhibitor chaperone with pan-retroviral activity suggests a broader insight into host cell defenses. Again, not intended to be bound in theory, the identification here of Pin1 as a chaperone that inhibits retroviruses suggests that the link between chaperones and host cell restriction is not a fluke. Chaperones such as Pin1 form a "morphogenic defense" that alters incoming retroviral capsids into a subset of structures that can be recognized by existing restriction factors. Forcibly adapting the antigen to be recognizable by existing intracellular defenses via chaperones could compensate for the rapid evolution of retroviruses relative to hosts. It would obviate the need to produce restriction factors that anticipate the morphology of every possible incoming viral antigen. In addition, the period between viral entry and integration is brief. Proximity between chaperone and restriction factor, so that "correct shapes" are instantly recognized, would be advantageous, possibly driving selective pressures that link chaperones and restriction factors together genetically.

IV. Inhibiting Enzymatic Activity or Expression of Parvulin Prolyl Peptidyl Isomerases Employing inhibitors of the parvulin family peptidyl prolyl isomerases such as Pin1, the invention provides methods for enhancing infectivity of a retroviral vector or recombinant retrovirus. Any compounds that specifically inhibit a parvulin peptidyl prolyl isomerase can be used in the invention. These include compounds known in the art to antagonize or inhibit the isomerase activity of a parvulin PPIase. They also encompass novel parvulin PPIase inhibitors that can be identified in accordance with screening assays routinely practiced in the art.

In some preferred embodiments, the invention employs known antagonist compounds of a parvulin PPIase (e.g., Pin1) that have been well characterized in the art. Examples of such inhibitors include, e.g., PiB and Juglone (Uchida et al., Chem. Biol. 10:15-24, 2003; and Chao et al., Nuc. Acids. Res. 29:767-73, 2001). These compounds can be either obtained commercially or synthesized in accordance with schemes reported in the art. PiB, diethyl-1,3,6,8-tetrahydro-1,3,6,8-tetraoxobenzo[lmn][3,8]phenanthroline-2,7-diacetate, inhibits Pin1 PPIase activity in vitro with low mM IC50s and has little nonspecific toxicity. The antagonist activity of PiB on the parvulin family peptidyl prolyl isomerases was well documented in the art (see, e.g., Uchida et al., Chem. Biol. 10:15-24, 2003). Juglone, 5-hydroxy-1,4-naphthoquinone, inhibits the members of the parvulin PPIase family and functions by modifying sulfhydryl groups (Hennig et al., Biochemistry 37:5953-5960, 1998). It was shown that juglone inactivates the *E. coli* PPIase, parvulin, by covalent modification of two cysteine residues in a slow process. The activity of members of the other PPIase families is not affected by juglone at all.

In addition to PiB and Juglone, other antagonist compounds of parvulin PPIases known in the art can also be employed in the practice of the present invention. These include, e.g., PiA (2,7-dimethylbenzo[lmn][3,8]phenanthroline-1,3,6,8 (2H,7H)-tetrone) and PiJ (diethyl-1,3,8,10-tetrahydro-1,3,8,10-tetraoxoanthra[2,1,9-def:6,5,10-d'e'f']diisoquinoline-2,9-diacetate). These compounds were also shown to potently inhibit the PPIase activity of Pin1 (Uchida et al., Chem. Biol. 10:15-24, 2003). Many other inhibitors of parvulin PPIases (e.g., Pin1) disclosed in the art can also be used in the practice of the invention. There include, e.g., Ac-Phe-D-Thr(PO3H2)-Pip-Nal-Gln-NH2 (Wildemann et al., J. Biol. Chem. 388:1103-11, 2007), Fmoc-(bisPOM)-pSer-Psi[(Z)CHC]-Pro-(2)-N-(3)-ethylaminoindole (Zhao et al., Bioorg. Med. Chem. Lett. 17:6615-8, 2007), Aryl 1-indanyl ketones (Daum et al., J. Med. Chem. 49:2147-50, 2006), and peptide inhibitors of human Pin1 (Wildemann et al., J. Med. Chem. 49:2147-50, 2006), In some other embodiments of the invention, novel compounds that specifically antagonize or inhibit the isomerase activity of parvulin PPIases can be employed. Such antagonist compounds of parvulin peptidyl prolyl isomerases can be identified using assays routinely practiced in the art. For example, chemical compound libraries can be screened in vitro for compounds that inhibit the peptidyl prolyl isomerase activity of a given parvulin family peptidyl prolyl isomerase (e.g., Pin1) as described in Yaffe et al., Science 278:1957-60, 1997; and Uchida et al., Chem. Biol. 10:15-24, 2003. The library of compounds can be one comprised of a randomly synthesized chemical compounds, peptide compounds or compounds of other chemical nature. The library can also comprise compounds that are derived from known inhibitors of a parvulin PPIase, e.g., PiB or Juglone. As an exemplification, the library of candidate compounds can be incubated with the parvulin PPIase (e.g., Pin1) in the presence of a labeled substrate of the enzyme, e.g., a MCA conjugated peptide substrate. Inhibitory effect of the candidate compounds on the PPIase activity can be monitored by measuring the MCA fluorescence as described in Uchida et al., Chem. Biol. 10:15-24, 2003.

Instead of using a compound that inhibits the enzymatic activity of a parvulin PPIase, some other embodiments of the invention employ a producer cell that has suppressed or diminished expression of a functional parvulin PPIase (e.g., human Pin1). This can be accomplished by knocking out the gene encoding the parvulin PPIase (e.g., a Pin1 knock-out cell line). The producer cell can also have mutations introduced into the gene that disrupts its enzymatic activities via site-directed mutagenesis (e.g., Pin1 W34A or Pin1R68,69A mutants as exemplified in the Examples below). Producer cells with an endogenous parvulin PPIase gene being knocked out or site specifically mutated can be generated using methods well known in the art. Such methods are described in, e.g., Sambrook et al., *Molecular Cloning: A Laboratory Manual*, Cold Spring Harbor Press (3$^{rd}$ ed., 2001); and Brent et al., *Current Protocols in Molecular Biology*, John Wiley & Sons, Inc. (ringbou ed., 2003). Further, in addition to cell lines with inhibited or suppressed expression of a parvulin PPIase, the producer cell lines to be employed in the invention can also be cells engineered to transiently or constitutively express at least one peptide inhibitor of a parvulin PPIase. As noted above, such peptide inhibitors are well known in the art.

Moreover, rather than having permanently altered Pin1 expression, the producer cell can also be one in which expression of the parvulin PPIase is transiently suppressed or inhibited. This can be achieved by, e.g., an inhibitory polynucleotide molecule that specifically targets the parvulin PPIase (e.g., Pin1 in a human cell). Examples of inhibitory polynucleotides that target the parvulin PPIase include, e.g., short interfering RNAs (siRNAs), microRNAs (miRNAs), short hairpin RNAs (shRNAs), anti-sense nucleic acids, and complementary DNAs (cDNAs). Using any of these nucleic acid agents to specifically silence expression of a target gene has been well known and routinely practiced in the art. Interference with the function and expression of endogenous genes by double-stranded RNA has been shown in various organisms such as *C. elegans* as described, e.g., in Fire et al., Nature 391:806-811, 1998; *drosophila* as described, e.g., in Kennerdell et al., Cell 95:1017-1026, 1998; and mouse embryos as described, e.g., in Wianni et al., Nat. Cell Biol. 2:70-75, 2000.

Inhibitory nucleic acid agents that specifically target a parvulin PPIase (e.g., Pin1) can be prepared using methods well known in the art. In general, such double-stranded RNA can be synthesized by in vitro transcription of single-stranded RNA read from both directions of a template and in vitro annealing of sense and antisense RNA strands. Double-stranded RNA can also be synthesized from a cDNA vector construct in which a parvulin PPIase gene is cloned in opposing orientations separated by an inverted repeat. Following cell transfection, the RNA is transcribed and the complementary strands reanneal. Double-stranded RNA targeting a parvulin PPIase gene can be introduced into a cell by transfection of an appropriate construct. By way of example, synthesis of a specific shRNA targeting Pin1 and its activity in suppressing Pin1 expression are described in the Examples below. Use of inhibitory polynucleotides to silence or suppress expression of a parvulin PPIase (e.g., Pin1) has also been disclosed extensively in the art. See, e.g., Yi et al., Mol. Cell. Biol. 25:9687-99, 2005; Pang et al., J. Pathol. 210:19-25, 2006; Xu et al., Mol. Cell. 26:287-300, 2007; Ding et al., Cancer Res. 68:6109-17, 2008; and Lam et al., Mol. Cancer. 15:7:91, 2008. Further, Pin1 targeting inhibitory polynucleotides such as siRNAs or shRNAs can be readily generated with kits available from various commercial sources. These include, e.g., Dharmacon (Chicago, Ill.), Santa Cruz Biotechnology (Santa Cruz, Calif.) and Invitrogen (Carlsbad, Calif.).

V. Producing Recombinant Retroviruses with Enhanced Infectivity

The invention provides methods for enhancing infectivity of retroviral vectors or recombinant retroviruses used for gene transfer in many settings. Retroviral vectors or recombinant retroviruses are widely employed in gene transfer in various therapeutic or industrial applications. For example, gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, Science 256:808-813, 1992; Nabel & Feigner, TIBTECH 11:211-217, 1993; Mitani & Caskey, TIBTECH 11:162-166, 1993; Mulligan, *Science* 926-932, 1993; Dillon, TIBTECH 11:167-175, 1993; Miller, Nature 357:455-460, 1992; Van Brunt, *Biotechnology* 6:1149-1154, 1998; Vigne, *Restorative Neurology and Neuroscience* 8:35-36, 1995; Kremer & Perricaudet, *British Medical Bulletin* 51:31-44, 1995; Haddada et al., in *Current Topics in Microbiology and Immunology* (Doerfler & Böhm eds., 1995); and Yu et al., *Gene Therapy* 1:13-26 (1994)).

The retroviruses are a group of single-stranded RNA viruses characterized by an ability to convert their RNA to double-stranded DNA in infected cells by a process of reverse-transcription. The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These elements contain strong promoter and enhancer sequences and are also required for integration in the host cell genome.

In order to construct a retroviral vector for gene transfer, a nucleic acid encoding a gene of interest is inserted into the viral genome in the place of certain viral sequences to produce a viral construct that is replication-defective. In order to produce virions, a producer host cell or packaging cell line is employed. The host cell usually expresses the gag, pol, and env genes but without the LTR and packaging components. When the recombinant viral vector containing the gene of interest together with the retroviral LTR and packaging sequences is introduced into this cell line (e.g., by calcium phosphate precipitation), the packaging sequences allow the RNA transcript of the recombinant vector to be packaged into viral particles, which are then secreted into the culture media. The media containing the recombinant retroviruses is then collected, optionally concentrated, and used for gene transfer.

Suitable host or producer cells for producing recombinant retroviruses or retroviral vectors according to the invention are well known in the art. Many retroviruses have already been split into replication defective genomes and packaging components. For other retroviruses, vectors and corresponding packaging cell lines can be generated with methods routinely practiced in the art. The producer cell typically encodes the viral components not encoded by the vector genome such as the gag, pol and env proteins. The gag, pol and env genes may be introduced into the producer cell and stably integrated into the cell genome to create a packaging cell line. The retroviral vector genome is then introduced-into the packaging cell line by transfection or transduction to create a stable cell line that has all of the DNA sequences required to produce a retroviral vector particle. Another approach is to introduce the different DNA sequences that are required to produce a retroviral vector particle, e.g. the env coding sequence, the gag-pol coding sequence and the defective retroviral genome into the cell simultaneously by transient triple transfection. In some preferred embodiments of the invention, both the structural components and the vector genome will all be encoded by DNA stably integrated into a host cell genome.

Typically, the methods of the invention involve transfecting a retroviral vector into a host cell or packaging cell line that has suppressed expression or enzymatic activity of an endogenous parvulin PPIase, and culturing the host under suitable conditions so that retroviral particles encapsulating the vector are produced. In some embodiments, the viral particles can be produced from the host cell in the presence of an inhibitor compound of parvulin PPIases (e.g., human Pin1). For example, as demonstrated in the Examples below, PiB or Juglone can be used to inhibit Pin1 in a human host cell such as HEK 293 cell line or HEK 293T cell line. The host cell can be transfected with the viral vector in the presence of the inhibitor compound. The host cell can also be pre-treated with the inhibitor compound prior to transfection with the viral vector. The host cell can also be transfected with the viral vector, and then cultured for production of viral particles in the presence of the inhibitor compound.

In some other embodiments, instead of inhibiting the isomerase activity of the parvulin PPIase with an antagonist compound, the host cell used for producing the viral particles can also have suppressed expression of the parvulin PPIase. As described above, this can be achieved by permanently depleting expression of the parvulin PPIase (e.g., with a human Pin1 knockout cell line) or transiently inhibiting expression of the enzyme (e.g., treating the host cell with an inhibitory nucleic acid targeting Pin1, such as a shRNA). When an inhibitory polynucleotide is utilized, the host cell can be co-transfected with the viral vector and the inhibitory polynucleotide. The host cell can also be pretreated with the inhibitory polynucleotide prior to transfection with the viral vector.

The methods of the invention can be practiced with various retroviral vectors and packaging cell lines well known in the art. Particularly suitable for the present invention are lentiviral vectors. Lentiviral vectors are retroviral vector that are able to transducer or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731-2739, 1992; Johann et al., *J. Virol.* 66:1635-1640, 1992; Sommerfelt et al., *Virol.* 176:58-59, 1990; Wilson et al., *J. Virol.* 63:23742378, 1989; Miller et al., *J. Virol.* 65:2220-2224, 1991; and PCT/US94/05700).

In particular, a number of viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent. pLASN and MFG-S are examples are retroviral vectors that have been used in clinical trials (Dunbar et al., *Blood* 85:3048-305 (1995); Kohn et al., *Nat. Med.* 1:1017-102 (1995); Malech et al., *Proc. Natl. Acad. Sci. U.S.A.* 94:22 12133-12138 (1997)). PA317/pLASN was the first therapeutic vector used in a gene therapy trial. (Blaese et al., *Science* 270:475-480, 1995). Transduction efficiencies of 50% or greater have been observed for MFG-S packaged vectors (Ellem et al., *Immunol Immunother.* 44:10-20, 1997; Dranoff et al., *Hum. Gene Ther.* 1:111-2, 1997).

Many producer cell line or packaging cell line for transfecting retroviral vectors and producing viral particles are also known in the art. The producer cell to be used in the invention needs not to be derived from the same species as that of the target cell (e.g., human target cell). For example, the present inventors observed that infectivity of retroviruses produced in Pin1-suppressed simian cells is similarly enhanced relative to that of viruses produced in Pin1-suppressed human produce cells. This indicates that blocking simian Pin1 has the same effect as blocking human Pin1 in enhancing viral infectivity. Accordingly, producer or packaging cell lines suitable for the present invention include cell lines derived from human (e.g., HEK 292 cell), monkey (e.g., COS-1 cell), mouse (e.g., NIH 3T3 cell) or other species (e.g., canine). Some of the cell lines are disclosed in the Examples below. Additional examples of retroviral vectors and compatible packaging cell lines for producing recombinant retroviruses in gene transfers are reported in, e.g., Markowitz et al., *Virol.* 167:400-6, 1988; Meyers et al., *Arch. Virol.* 119:257-64, 1991 (for spleen necrosis virus (SNV)-based vectors such as vSNO21); Davis et al., *Hum. Gene. Ther.* 8:1459-67, 1997 (the "293-SPA" cell line); Povey et al., *Blood* 92:4080-9, 1998 (the "1MI-SCF" cell line); Bauer et al., *Biol. Blood Marrow Transplant.* 4:119-27, 1998 (canine packaging cell line "DA"); Gerin et al., *Hum. Gene Ther.* 10:1965-74, 1999; Sehgal et al., *Gene Ther.* 6:1084-91, 1999; Gerin et al., *Biotechnol. Prog.* 15:941-8, 1999; McTaggart et al., *Biotechnol. Prog.* 16:859-65, 2000; Reeves et al., *Hum. Gene. Ther.* 11:2093-103, 2000; Chan et al., *Gene Ther.* 8:697-703, 2001; Thaler et al., *Mol. Ther.* 4:273-9, 2001; Martinet et al., *Eur. J. Surg. Oncol.* 29:351-7, 2003; and Lemoine et al., *I. Gene Med.* 6:374-86, 2004. Any of these and other retroviral vectors and packaging producer cell lines can be used in the practice of the present invention.

Many of the retroviral vectors and packing cell lines used for gene transfer in the art can be obtained commercially. For example, a number of retroviral vectors and compatible packing cell lines are available from Clontech (Mountain View, Calif.). Examples of lentiviral based vectors include, e.g., pLVX-Puro, pLVX-IRES-Neo, pLVX-IRES-Hyg, and pLVX-IRES-Puro. Corresponding packaging cell lines are also available, e.g., Lenti-X 293T cell line. In addition to lentiviral based vectors and packaging system, other retroviral based vectors and packaging systems are also commercially available. These include MMLV based vectors pQCXIN, pQCXIQ and pQCXIH, and compatible producer cell lines such as HEK 293 based packaging cell lines GP2-293, EcoPack 2-293 and AmphoPack 293, as well as NIH/3T3-based packaging cell line RetroPack PT67. Any of these and other retroviral vectors and producer cell lines can be employed in the practice of the present invention.

Culturing a retroviral vector in a packaging cell line with inhibited or suppressed parvulin PPIase activity or expression can be carried out in accordance with protocols well known in the art or that exemplified in the Examples below. For example, when a chemical compound inhibitor (e.g., PiB or Juglone) is used, the producer or packaging cell can be pretreated with the inhibitor compound prior to transfection with the retroviral vector. Alternatively, the producer cell can be transfected with the viral vector in the presence of the compound. The concentration of the inhibitor compound to be used can be easily determined and optimized by the skilled artisans, depending on the nature of the compound (e.g., an organic chemical compound or a nucleic acid compound), the vector and producer cell being used, as well as when the cell is contacted with the inhibitor compound (prior to or simultaneously with transfection with the vector). Typically, the inhibitor compound should present in a range from about 10 nM to about 2 mM. Preferably, the inhibitor compound used in the methods is at a concentration of from about 50 nM to about 500 µM, from about 100 nM to 100 µM, or from about 0.5 µM to about 50 µM. More preferably, the inhibitor compound is contacted with the producer cell at a concentration of from about 1 µM to about 20 µM, e.g., 1 µM, 2 µM, 5 µM or 10 µM.

VI. Gene Transfer Via Recombinant Retroviruses with Enhanced Infectivity

The methods of the present invention can be used to enhance infectivity of recombinant retroviruses expressing various exogenous genes. For example, recombinant retroviruses with enhanced infectivity and transduction efficiency can be produced to transfer an exogenous gene or heterologous polynucleotide sequence in gene therapy and agricultural bioengineering applications. For any given gene to be transferred, a recombinant retroviral vector can be readily constructed by inserting the gene operably into the vector, replicating the vector in an appropriate packaging cell with inhibited or suppressed parvulin PPIase expression or activity, obtaining viral particles produced therefrom, and then infecting target cells with the recombinant viruses.

The recombinant retroviruses expressing an exogenous gene can be transduced into any target cells for recombinant expression of the exogenous gene. Preferred target cells for the present invention include, but are not limited to, cells derived from both human and non-human animals including vertebrates and mammals. Specific examples of target cells include that originate from bovine, ovine, porcine, canine, feline, avian, bony and cartilaginous fish, rodents including mice and rats, primates including human and monkeys, as well as other animals such as ferrets, sheep, rabbits and guinea pigs. In addition, the target cells can also be plant cells, e.g., a cell from a crop, for generation of genetically modified plants or crops. Thus, other than the various animal retroviruses discussed above, the gene transfer can also employ a vector that is derived from plant retroviruses. Any of the plant retroviruses well known in the art can be used and adapted in the practice of the present invention. See, e.g., Grandbastien et al., Nature 337:376-80, 1989; Yano et al., BMC. Evol. Biol. 5:30, 2005; and Pearce, Cell Mol. Biol. Lett. 12:120-6, 2007.

The methods of the invention can be employed in the transfer and recombinant expression of various exogenous genes or heterologous polynucleotide sequences. Typically, the gene or heterologous polynucleotide sequence is derived from a source other than the retroviral genome which provides the backbone of the vector used in the gene transfer. The gene may be derived from a prokaryotic or eukaryotic source such as a bacterium, a virus, a yeast, a parasite, a plant, or even an animal. The exogenous gene or heterologous polynucleotide sequence expressed by the recombinant retroviruses can also be derived from more than one source, i.e., a multigene construct or a fusion protein. In addition, the exogenous gene or heterologous polynucleotide sequence may also include a regulatory sequence which may be derived from one source and the gene from a different source.

The exogenous gene or heterologous polynucleotide sequence harbored by the recombinant retrovirus can simply encode a protein for which large quantities of the protein are desired, i.e., large scale in vitro production methods. Alternatively, the gene could be a therapeutic gene, for example to treat cancer cells, to express immunomodulatory genes to fight viral infections, or to replace a gene's function as a result of a genetic defect. The exogenous gene expressed by the recombinant retrovirus can also encode an antigen of interest for the production of antibodies. For agricultural applications, the exogenous gene to be transferred into a target plant cell can be any gene that encodes a polypeptide that confers a desirable characteristic on the plant. For example, the exogenous gene can encode a polypeptide that improves the nutritional or ornamental value of the transgenic plant. The gene can also encode a polypeptide that provides enhanced resistance to stress conditions (e.g., thermal or osmotic stress).

In some exemplary embodiments, the exogenous gene to be transferred with the methods of the present invention is a gene that encodes a therapeutic polypeptide. For example, transfection of tumor suppressor gene p53 into human breast cancer cell lines has led to restored growth suppression in the cells (Casey et al., Oncogene 6:1791-7, 1991). In some other embodiments, the exogenous gene to be transferred with methods of the present invention encodes an enzyme. For example, the gene can encode a cyclin-dependent kinase (CDK). It was shown that restoration of the function of a wild-type cyclin-dependent kinase, p16INK4, by transfection with a p16INK4-expressing vector reduced colony formation by some human cancer cell lines (Okamoto, Proc. Natl. Acad. Sci. U.S.A. 91:11045-9, 1994). Additional embodiments of the invention encompass transferring into target cells exogenous genes that encode cell adhesion molecules, other tumor suppressors such as p21 and BRCA2, inducers of apoptosis such as Bax and Bak, other enzymes such as cytosine deaminases and thymidine kinases, hormones such as growth hormone and insulin, and interleukins and cytokines.

The invention also provides pharmaceutical combinations, e.g. kits, that can be employed to carry out the various methods disclosed herein. Such pharmaceutical combinations typically contain an active inhibiting-agent which is an inhibitor of a parvulin PPIase (e.g., Pin1), in free form or in a composition with one or more inactive agents, and other components. For example, the kits of the invention can contain one of the various Pin1 inhibitors disclosed here (e.g., PiB). The inhibiting-agent can also be a compound that suppresses expression or cellular level of the parvulin prolyl peptidyl isomerase, e.g., a siRNA or shRNA molecule or expression construct as exemplified herein. The kits can additionally contain instructions or an instruction sheet detailing how to use the inhibiting agent and an appropriate packaging or producer cell line (which may or may not be included in the kits) to produce retroviruses with enhanced infectivity. The kits can further contain a packaging or producer cell line (e.g., 293T cell line) which expresses the parvulin prolyl peptidyl isomerase (e.g., Pin1).

In some related embodiments, the kits contain a modified producer cell line into which the inhibiting agent has already been introduced. For example, the kits can contain (1) a retroviral producer cell line which has a parvulin PPIase (e.g., Pin1) stably knocked-out or knocked-down and (2) an instruction for using the cell line in producing viruses with enhanced infectivity. Such a cell line can be readily generated using standard techniques in molecular biology or protocols exemplified herein. In various embodiments, the pharmaceutical combinations or kits of the invention can optionally further contain one or more appropriate retroviral vectors (e.g., a vector described above) for cloning a target gene of interest and producing recombinant viruses with enhanced infectivity.

EXAMPLES

The following examples are provided to further illustrate the invention but not to limit its scope.

Example 1

Materials and Methods

This Example describes some of the materials and methods employed in the studies described below.

Vector construction. The dgal signal sequence was ligated into the pCGMT phagemid between EcoRI and HindIII restriction sites, which in turn also removed the pelB signal sequence. Influenza hemagglutinin (residues 11-329 (HA1) and 1-176 (HA2) of the ectodomain of hemagglutinin from A/Vietnam/1203/2004) was amplified by PCR and ligated into dgal-pCGMT between a 5' XmaI restriction site and 3' SfiI restriction site to generate the desired dgal-HA insert into pCGMT.

Plasmids: Laboratory-adapted provirus NL4.3, and the CypA-independent NL4.3 CAi2 were kindly provided by Akio Adachi (Department of Virology, Institute of Health Biosciences, The University of Tokushima Graduate School, JAPAN). Mutant R9G89V was a gift from P. Gallay (TSR1) as were NL4.3-GFP and SIV-GFP (originally Dana Gabuzda, Dana Farber Cancer Institute). NL4.3 A92E was kindly provided by W. Phares (Genetics Unit, Novartis Forschungsinstitut, Vienna, Austria). R9Δgp160 plasmid clone was kindly provided by C. Aiken (Vanderbilt Medical Center). VSV-G (CMV-VSV-G) was kindly provided by D. Trono (École Polytechnique Fédérale de Lausanne). Both bMLV-GFP and nMLV-GFP in the form of pCIG3-N, pCIG3-B as well as pCNCG were kindly provided by J. Stoye (National Institute for Medical Research, UK). Isomerase mutant Pin1 (pFLAG-Pin1R68,69A) and WW-domain mutant Pin1 (pFLAG-Pin1 W34A) were constructed by site-directed mutagenesis. Pseudotyping experiments were performed using DNA constructs encoding the VSV-G generously provided by D. Trono. Human Pin1 was cloned into pFLAG (Sigma-Aldrich) making pFLAG-Pin1. Viruses were produced by transfection of 293T cells using either GeneJuice (Novagen) or calcium phosphate. It is important to note calcium phosphate transfections require larger amounts of DNA, which although generally undesirable, happened to provide greater flexibility when altering the ratio of Pin1 to proviral construct than when GeneJuice was used. All viruses were harvested 24-48 hours post-transfection and filtered (0.2-μM filter, Steriflip Millipore). HIV-1 viruses were normalized by p24 ELISA (Alliance HIV-1 p24 Antigen ELISA Kit, Perkin Elmer), and/or were normalized via the EnzChek® Reverse Transcriptase Assay Kit (E-22064) (Molecular Probes).

Cell Lines and PBMCs: The TZM-bl cell line was obtained through the NIH AIDS Research and Reference Reagent Program, Division of AIDS, NIAID, NIH: TZM-bl from Dr. John C. Kappes, Dr. Xiaoyun Wu and Tranzyme Inc. The sMAGI cell line was obtained through the AIDS Research and Reference Reagent Program, Division of AIDS, NIAID, NIH: CMMT-CD4-LTR-β-Gal (sMAGI) from Dr. Julie Overbaugh. African green kidney BS-C-1 CCL-26, African green kidney CV-1 CCL-70, African green kidney Vero CCL-81, owl kidney OMK(637-69) CRL-1556 and 293T cell lines were obtained from ATCC. To generate PBMCs, human blood from normal healthy donors (General Clinical Research Center, TSR1) was fractionated via gradient centrifugation through histopaque-1077 (Sigma-Aldrich). Peripheral blood lymphocytes (PBLs) were cultured in RPMI supplemented with 20% FBS, 20 U ml$^{-1}$ IL-2.

Inhibitors: Diethyl-1,3,6,8-tetrahydro-1,3,6,8-tetraoxobenzo[lmn][3,8]phenanthroline-2,7-diacetate (also termed PiB), (EMD Biosciences, Inc.) and 5-hydroxy-1,4-naphthoquinone (also termed juglone) (Sigma) were prepared in either EtOH or DMSO 0.5-2 mg ml$^{-1}$, following manufacturer's recommendations.

Infection assays for retrovirus: Single-round infections: CD4$^+$ TZM-bl 100,000 cells/well/mL were seeded onto 24-well plates 24 hours prior to infection. These cells were infected in quadruplicate to 24-well plates. Infectivity was scored using an enzymatic galactosidase activity assay. Specifically, infected TZM-bl cells were washed and lysed, and 20 μl of lysate was transferred to a 96-well plate for detecting β-galactosidase activity. 100 μl of reaction buffer Galacton-Star substrate (Applied Biosystems, Bedford, Mass.), diluted 1:50, was added to 20 μl of lysate, and the light emission was measured over 1 second in a microplate luminometer after 30 minutes incubation. For human PBMC infections, cells were exposed to 10 ng of wild-type virus for 6 hours, washed, and split into two flasks: one with 10 μM PiB added on day 0 and 3, and one without PiB. Replication was monitored by p24 ELISA. For measuring infectivity of GFP-virus, 50,000 TZMb1, sMAGI, OMK, Vero, BSC-1 and CV-1 cells/well/mL were seeded onto 6-well plates respectively 24 hours prior to infection. Viruses were used to infect in duplicate wells, incubated for 48 hours, washed with PBS, trypsinized, fixed in 1% formaldehyde and subsequently analyzed by fluorescence-activated cell sorting (FACS) for percentage cells infected.

Infection assays for HCV: Persistently infected cells were treated with vehicle (DMSO), an MTP inhibitor (BMS-200150) capable of inhibiting HCV secretion, or with two doses of PiB (16 μM and 8 μM). After 1 hour of pre-treatment at 37° C., cells were washed with warm PBS and further incubated in normal medium containing the same inhibitors for an additional 9 hours at 37° C. Cell supernatants containing infectious HCV were collected for infectivity titer determination. These particles were assembled and secreted de novo during the time the cells were exposed to the drugs, as shown by the virtual absence of particles in cells treated with the HCV assembly inhibitor BMS-200150. Note that Pin1 is able to block HIV-1 in the HUH-7 cell line used to propagate HCV.

Immunoblots: Whole-cell extracts were normalized by BCA assay (Bio-Rad), resolved by SDS-polyacrylamide gel electrophoresis (PAGE), transferred to PVDF membranes and probed using rabbit anti-Flag (ABR) or rabbit anti-Pin1 antibody Pin1 (H-123) Antibody sc-15340 (Santa Cruz Biotechnology, Inc.) Rabbit anti-capsid antiserum to HIV-1 p24 (Cat #287) and antisera to HIV-1 p17 (Cat #286), HIV-1 gp120 (Cat #288), HIV-1 Protease (Cat #4105), and HIV-1 RT (Cat #6195) were obtained through the AIDS Research Reference and Reagent Program.

Example 2

Inhibition of Pin1 Isomerase in HIV-1 Producer Cells Boosts Virion Infectivity

To examine a potential role for Pin1 in HIV-1 replication we used two inhibitors of Pin1: juglone and PiB. They do not inhibit other prolyl isomerases such as CypA or FKBP, and act via a distinct mechanisms. 293T cells were transfected with a proviral construct encoding wild-type HIV-1 in the presence or absence of PiB or juglone. PiB had no effect on the producer cell viability as measured by cell count and trypan blue staining (data not shown). Resultant viral supernatants, normalized to equivalent particle number, were used to infect target cells (TZM-bl Hela cell). Neither inhibitor influences viral production (FIG. 1a). Remarkably we found a 2-fold boost of infectivity with viruses produced in the presence of 2.0 μM PiB or 2 μM juglone, and an 8-fold boost with viruses treated with 10 μM PiB (FIG. 1b). Interestingly, infectivity of a VSV-G pseudotyped of HIV-1 mutant lacking the gp160 gene (NL4.3 Δenv) is also enhanced by inhibition of Pin1 (FIG. 1c). Since VSV-G pseudotyped HIV-1 bypasses both the CD4 and chemokine receptors normally used by HIV-1 to enter cells, Pin1 apparently does not influence attachment or entry into target cells. The small amount of drug carried over from viral supernatants to the target cells does not contribute to HIV-1 enhancement, as directly treating target cells with Pin1 inhibitors has no effect on infectivity (FIG. 1d). The lack of effect of Pin1 on the target cell is distinct from CypA, which has been reported to act both in the producer cell and perhaps more predominantly, in the target cell. The observed enhancement of viral infectivity caused by inhibiting Pin1 in the producer cell suggests that either (1) these drugs directly boost an activity important for HIV-1 infectivity, or (2) these drugs block an inhibiting effect on HIV-1.

To assess the effect of Pin1 inhibition in a more physiological context, we examined the effect of inhibiting Pin1 on HIV-1 infectivity in human peripheral blood lymphocytes (PBLs). PBLs were isolated and challenged with HIV-1 in the presence or absence of Pin1 isomerase inhibitors. Consistent with our findings in HeLa cells, inhibition of Pin1 enhanced HIV-1 replication in PBLs (FIG. 1e). Peak replicative differential was observed on day 5 (0.2 μg/ml p24 untreated versus 1.4 μg/ml p24) representing a seven-fold increase in infectivity due to the inhibition of Pin1. The fact that this differential is not maintained may be due to PiB instability at 37° (13). We conclude that blocking Pin1 isomerase in human PBLs significantly enhances HIV-1 replication kinetics. We believe this is the first demonstration of a known human protein inhibiting wild-type HIV-1 under physiological conditions.

Because drug treatment may have indirect effects, we asked whether genetically knocking down Pin1 expression in producer cells using shRNA would have the same effect as pharmaceutical treatment with Pin1 inhibitors. The shRNA construct targeting human Pin1 was generated with pSilencer™ (Applied Biosystems, Carlsbad Calif.). The vector was digested with ApaI and EcorI, and then annealed with a target-specific oligonucleotide to generate a Pin1 shRNA construct and a control construct. Sequences of the oligonucleotides used in generating the constructs are:

```
Pin1 (SEQ ID NO: 1):
5'-gggcccGCCGAGTGTACTACTTCAAttcaagagaTTGAAGTAGTA

CACCTCGGCtttttttgattc-3';

Control (SEQ ID NO: 2):
5'-gggcccTCGTATGTTGTGTGGAATTttcaagagaAATTCCACACA

ACATACGAttttttgattc-3'.
```

The Pin1 specific shRNA-expressing vector (hPinpSil) was transfected into producer cells to assess its effect on activity of viruses produced therefrom. In order to maintain the same total amount of DNA in each transfection, 293T cells were transfected with 20 μg control pSilencer vector, or increasing amounts of the Pin1-specific shRNA hPin1pSil (1 μg+19 μg control, 5 μg+15 μg control, 10 μg+10 μg control or 20 μg straight Pin1-specific shRNA). Results from the study are shown in FIG. 1. First, it was found that Pin1-specific shRNA reduced the amount of endogenous Pin1 within 293T producer cells (lysates taken at time of viral harvest) but did not alter the expression of α-tubulin (FIG. 1f). Importantly, virions produced from these shRNA-treated cells exhibited nearly a 10-fold boost of infectivity (FIG. 1f), corroborating our previous observation that pharmaceutical inhibition of Pin1 isomerase boosts HIV-1 infection. Altogether our findings show 1) a direct correlation between HIV-1 infectivity and endogenous levels of Pin1 in producer cells. Thus, Pin1 specifically decreases HIV-1 infectivity by acting on virions in the producer cell. Overall, our data show that neutralizing Pin1 isomerase activity either via drug treatment or by genetic knockdown enhances HIV-1 infectivity, suggesting that endogenous Pin1 exerts an attenuating effect on HIV-1 infectivity.

Example 3

Overexpression of Pin1 in Producer Cells Inhibits HIV-1 Infectivity

Figure 2:
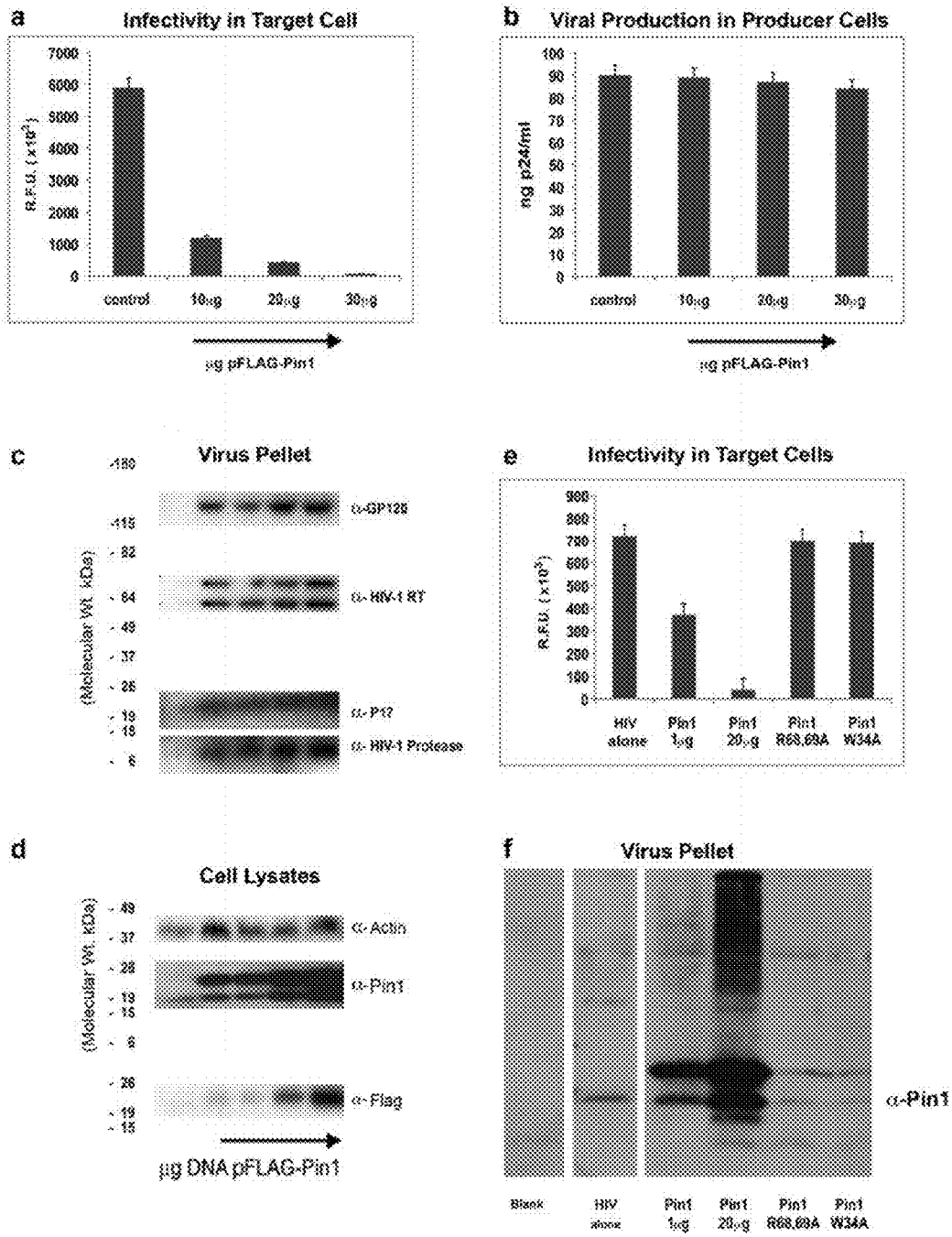

Given that blocking Pin1 isomerase activity boosts HIV-1 infectivity; we hypothesized that overexpression of Pin1 in producer cells should inhibit HIV-1 infectivity. To address this possibility, we cotransfected 293T cells with an HIV-1 proviral construct and a pFLAG-Pin1 expression vector or pFLAG, normalized virus via p24 ELISA and infected target cells as described above. We found that elevated Pin1 levels in producer cells do indeed inhibit HIV-1 in a dose-dependent manner (FIG. 2a), although overexpression of Pin1 has no effect on the number of virions produced (FIG. 2b). Taken together with our results above, we find that modulating the activity of Pin1 alone can govern HIV-1 activity over a range of at least 80-fold (8-fold boost of HIV-1 by inhibition of Pin1, at least 10-fold inhibition of HIV-1 by overexpression of Pin1). Thus, Pin1 is a specific and potent regulator of HIV-1 infectivity. It is interesting to note that the degree of inhibition observed is dependent on the multiplicity of infection (m.o.i.). At higher m.o.i.s, the relative inhibition of Pin1 diminishes.

Example 4

Pin1 Does not Alter the Relative Ratio of Key Viral Proteins

Although Pin1 has no effect on total viral production (FIG. 1b, 2b), we wondered if Pin1 activity alters the relative ratio of viral proteins that are important for HIV-1 infectivity. However, at levels of Pin1 expression that significantly reduce HIV-1 infectivity, we observe no effect on the relative ratio of gp120, reverse transcriptase, p17, and HIV-1 protease (FIG. 2c). Note that the level of expression of pFLAG Pin1 is dramatically higher than the endogenous Pin1 (FIG. 2d). We also saw no effect on the relative ratio of p55 to p24 suggesting that Pin1 does not influence maturation.

Example 5

The Isomerase Activity of Pin1 is Specifically Responsible for HIV-1 Inhibition

The fact that exogenously expressed Pin1 inhibits HIV-1 permits a direct means of testing whether either of two functional domains of Pin1(14) is required for inhibition. It is known that the point mutant W34A fully abrogates the WW-domain binding capacity of Pin1, and the R68,69A double mutant abrogates isomerase activity of Pin1. Plasmids containing these mutants were individually cotransfected with the wild-type HIV-1 proviral construct as above. We verified by western blot that both mutants are expressed at levels equal to that of to wild-type Pin1. Both mutants failed to inhibit HIV-1 (FIG. 2e). This suggests that inhibition is specific, and that both a functional isomerase domain and a functional WW domain are required for Pin1 to inhibit HIV-1.

Because it was previously shown that Pin1 is incorporated into HIV-1, we wondered if these mutations block Pin1 incorporation into HIV-1. We found that although our pFLAG Pin1 is incorporated into virions, neither W34A or R68,69A mutant is incorporated (FIG. 2f). It cannot be determined if Pin1 incorporation into HIV-1 actually causes inhibition. Many non-viral host proteins that are incorporated into HIV-1 are known to possess WW domains that could bind to Pin1, yet may play no role in retroviral replication. However, it can be said that Pin1 incorporation correlates with HIV-1 inhibition in a dose-dependent manner.

Example 6

Pin1 as a Pan-retroviral Inhibitor and Producer Species for Pin1 Antagonism

Figure 3:
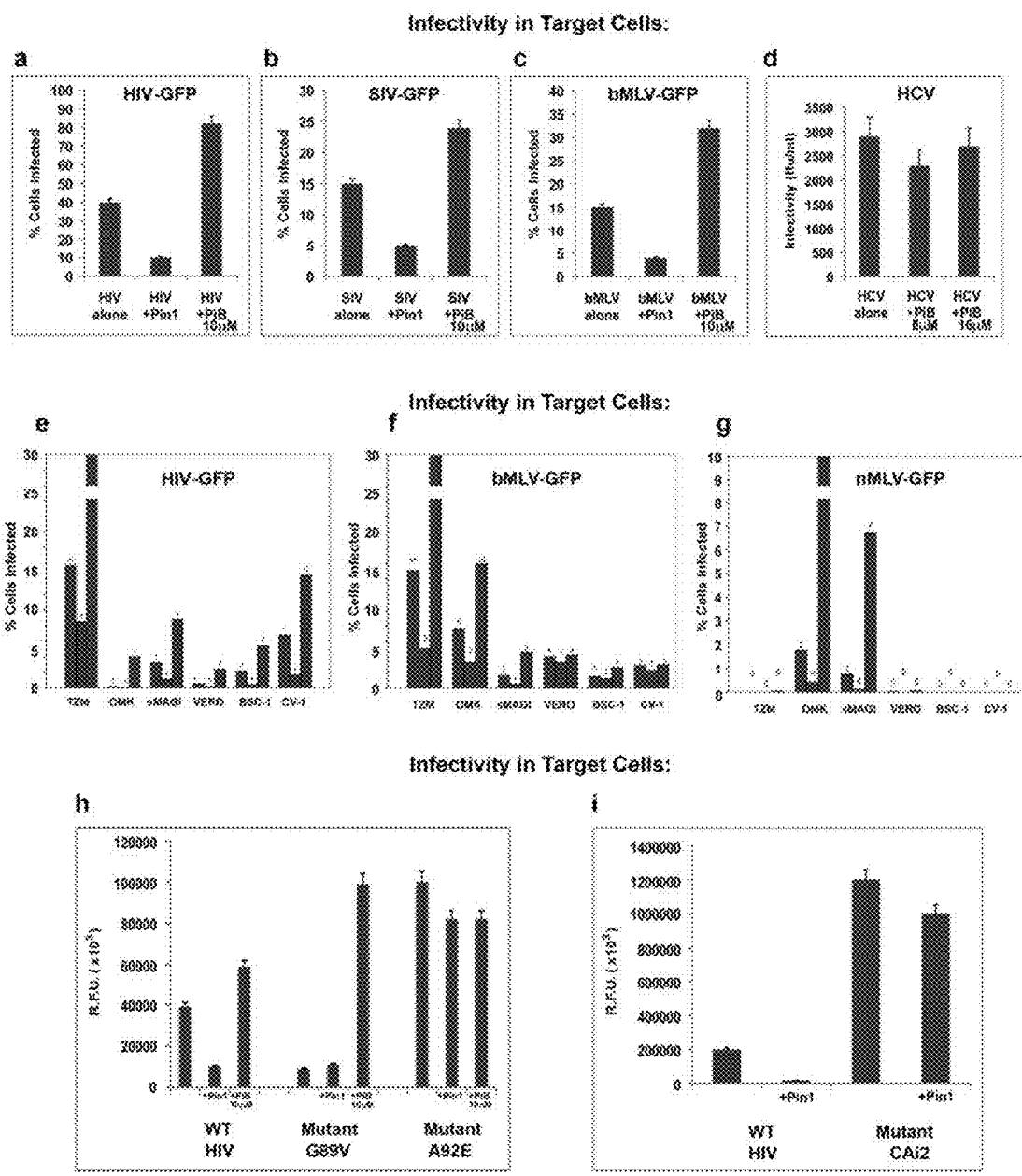

We next asked whether Pin1 influences the infectivity of other retroviruses such as SIV, bMLV and nMLV. Virions were produced in the presence or absence of PiB or excess Pin1 as described above. However, unlike previous experiments, virions were normalized via RT assay and infectivity in target cells was analyzed by GFP fluorescence via FACS. With the exception of nMLV, which failed to infect human cells, all showed the same response to Pin1: excess Pin1 inhibits all of these viruses, and Pin1 inhibitors boost their infectivity (FIG. 3a, b, c). Note that the observed effect of Pin1 on HIV-1 infectivity using a different means of normalizing viruses (reverse transcriptase activity vs. p24 capsid) and a different means of quantifying infectivity (GFP), agrees with our previous findings above. Overall, our findings suggest that Pin1 acts upon a mechanism common to these different retroviruses. Interestingly, we find that the flavivirus Hepatitis C (HCV) is not boosted by Pin1 isomerase inhibitors (FIG. 3d), suggesting that Pin1 targets a replicative step not utilized by HCV.

The above described experiments all relate to infectivity of viruses generated in Pin1-antagonized human producer cells. We asked if modulation of viral infectivity via Pin1 antagonism in the producer cell can be realized in different producer species, or if Pin1 modulates infectivity only when human cells are used as the producer cell. Thus, we examined the effect of Pin1 when viruses are produced from non-human primate cells. Specifically, HIV-1 and SIV were produced from 1) African green monkey-derived Vero and CV-1 cell lines, 2) the macaque-derived sMAGI cell line, and an 3) owl monkey cell line (OMK) as well as 4) human cells. All viruses were produced in the presence or absence of Pin1 inhibitors as described above. Identical inoculates, normalized for RT activity, were then used to infect human reporter cell lines. We found that despite the differing species origin of the produce cell, both infectivity of HIV-1 and SIV were boosted when the activity of Pin1 in these cells was blocked using Pin1 isomerase drug inhibitors. The results are consistent with the fact that simian Pin1 is very similar to human Pin1. These findings and the high degree of homology among Pin1s derived from different species suggest that any mammalian cells capable of producing retroviruses would likely produce viruses that are considerably more infectious when the endogenous Pin1 activity is blocked.

Example 7

Pin1 Amplifies Host Cell Restriction

We wondered if Pin1 inhibition is manifested in all target cells, suggesting the virus is "broken" in some way, or if Pin1 alters the interplay between incoming viruses and host in a manner that is target cell dependent. It is well established that the infectivity of many retroviruses is dependent on the species of the target cell. In many cases, this is due to activity of certain intracellular restriction factors (e.g., TRIM5α). Thus we compared the effect of Pin1 infectivity on retroviruses in target cells known to have different permissivities to these viruses. Specifically, HIV-1, nMLV, and bMLV were used to infect human cells, the Old World monkey cell lines (Vero, BSC-1, and CV-1, and sMAGI), and a New World monkey cell line (OMK). All viruses were produced in the presence or absence of Pin1 inhibitors, or excess Pin1 as described above. Identical inocula, normalized for RT activity, were used to infect each cell line. The infectivity of untreated viruses matches the known permissivities in these cells based on previous studies. Critically, identical viral inocula exhibited different responses to Pin1 depending on species of the target cell (FIG. 3e,f,g). For example, blocking Pin1 dramatically inhibited, and elevating Pin1 dramatically boosted, nMLV infectivity in sMAGI and OMK cells, yet showed no capacity to over-rule the restriction block of nMLV in human cells or African green monkey cells (FIG. 3g). More strikingly, the range of Pin1 influence (+/−) is approximately 6-fold in human, sMAGI and owl monkey cells, yet modulating Pin1 activity has no effect on bMLV infectivity in African green monkey cells (FIG. 3f). Interestingly, HIV-1 responded to Pin1 modulation over a 7-fold range or greater in all target cells (FIG. 3e). It is noteworthy that both owl monkey and macaque cell lines have been shown to have TRIM-CypA fusions which may offer a lead in future studies of Pin1 inhibition. These results define the nature of the Pin1 inhibitory effect on retroviruses: (1) Pin1 does not alter host cell "house-keeping" proteins essential for retroviruses; (2) Pin1 does not alter a fundamental function of the virus itself, (3) Pin1 activity amplifies pre-existing susceptibilities to restriction factors in the target cell.

Example 8

Pin1 and CypA have Opposing Effects on HIV-1 Infectivity

Host cell restriction of retroviruses is capsid-dependent. Further, the chaperone CypA, acts upon the HIV-1 capsid. The fact that CypA ameliorates HIV-1 infectivity raises the possibility that Pin1 and CypA are functional antagonists. If this were the case, then blocking Pin1 isomerase could rescue HIV-1 lacking CypA. To this end, we asked what effect Pin1 would have on HIV-1 containing a G89V point mutation in capsid, which disrupts the CypA-capsid interaction causing the virus to have diminished infectivity in human cells. Significantly, use of drugs that block Pin1 activity dramatically and disproportionately enhances CypA-deficient virus (11-fold), fully restoring HIV-1 infectivity to wild-type levels (FIG. 3h). Further, unlike wild-type HIV-1, overexpression of Pin1 does not further reduce the infectivity of the G89V mutant HIV-1. This suggests that blocking Pin1 alleviates an activity that contributes to the diminished infectivity of the G89V mutant normally observed in human cells.

We postulated that if CypA and Pin1 have antagonistic effects on HIV-1, HIV-1 mutants that have lost the requirement for CypA may have done so by becoming resistant to the depredations of Pin1. A number of HIV-1 capsid mutants are known to confer independence from CypA. We chose two: (1) a mutant (A92E) that arose from selective pressure on wild-type viruses grown in cyclosporine A (CsA, an inhibitor of CypA), and requires the presence of cyclosporine to replicate (37); and (2) a synthetic mutant (NL4.3CAi2) in which six amino acids of the CypA-binding loop of HIV-1 capsid are replaced by the corresponding amino acids from SIV capsid. NL4.3CAi2 does not require cyclosporine A to replicate. Importantly, we found that both A92E and NL4.3CAi2 were resistant to Pin1 inhibition, even at levels of Pin1 that inhibit wild-type virus (FIG. 3g,h). Taken together, these experiments show that (1) CypA and Pin1 have opposing effects on HIV-1 infectivity, and (2) since mutants in capsid protect HIV-1 from Pin1, capsid is likely to be a direct or indirect target of Pin1 inhibition.

Example 9

Enhanced Infectivity of HIV Produced in Cells with Stable Pin1 Knock-down

In previous experiments we have observed a boost of infectivity in viruses in cells whose Pin1 levels via transient shRNA knock-down. We then sought to generate a stable human knock-down cell line which would serve as a standardized basis. To that end, we used a pGIPZ system which permits the stable integration of vectors which continuously produce shRNAs, and can be maintained by antibiotics. Four anti-PIN1 Human pGIPZ shRNAmir (RHS4430-98520804; RHS4430-98903751; RHS4430-99292846; RHS4430-99329247) were transfected into human 293T cells. shRNA producers were stabilized by antibiotic selection. Intracellular expression of Pin1 was monitored via western blot and we observed significant diminishment of Pin1 in a number samples such as C-9, D-8, and F-2. These groups were further separated into subcultures such as F2-9 and F2-10 to provide more stable Pin1 knock down cell lines. 293T cells were transfected with a HIV-1 proviral construct (NL4-3). The resultant viral supernatants were normalized via p24 ELISA and used to infect human TZM reporter cells (target cells) in 24 well plates. Forty-eight hours later, infectivity was scored using the Galacton-Star enzymatic galactosidase activity assay and analyzed by luminometer, the y-axis representing relative fluorescence units. Note that the infectivity values shown are raw data that have not been averaged, thus there are no error bars. The results as shown in FIG. 4 indicate that viruses produced in cells with stable knocked-down Pin1 levels are more infectious than those produced in wild type cells.

Example 10

Enhanced Infectivity of SIV Produced in Cells with Pin1 Inhibition

In addition to HIV, we also examined effect of Pin1 suppression on infectivity of macaque SIV. Specifically, macaque SIV pseudotyped with VSV-G envelope were produced from human 293T cells which have been treated with Pin1 inhibitors and then analyzed for infectivity. The results are shown in FIG. 5. In brief, 293T cells were transfected with a SIV-GFP (Mac293), a CMV driven plasmid encoding VSV-G envelope protein alone, or in the presence of 2.0 µM PiB, 10.0 µM PiB, 20.0 µM PiB, or 40.0 µM PiB. Viral inoculates from the transfections above were normalized to equal virion particle number via RT assay. Infectivity was measured as GFP fluorescence via FACS. Each data point represents the sum of quadruplicates and the combination of three independent experiments. The results indicate that these viruses also exhibit enhanced infectivity in a dose dependent manner when produced from cells which have been treated with Pin1 inhibitors.

Example 11

Pin1 Inhibition Enhances HIV Replication Kinetics

PBLs from human donors were challenged with HIV-1 in the presence (squares) or absence (circles) of 10 µM PiB. Replication was monitored by sampling virus concentration in supernatants via p24 ELISA. Despite the fact that PiB breaks down in aqueous solution, and that fixed amounts of the drug are absorbed by the increased amounts of Pin1 produced in replicating cells, we observe significantly elevated kinetics (seven fold) after six days. It is likely that more stable inhibitors or to the addition of more drug would maintain this advantage. We interpret the delay of an effect until the third day as an indication that PiB does not increase initial virus production, and thus enhancement is only evidence after a round of infection occurs. The results shown in FIG. 6A indicate that Pin1 isomerase inhibitors can enhance replication kinetics of HIV-1 in human PBLs. The data shown represent the average p24 value of two independent donors.

In contrast to HIV, we also found that Pin1 isomerase inhibitor PiB does not enhance HCV infectivity (FIG. 6B). Persistently infected HUH-7 cells were treated with solvent DMSO (circles), or increasing concentrations of PiB (squares). After 1 hour of pre-treatment cells were washed and further incubated in normal medium containing the same inhibitors for an additional 9 hours at 37° C. Cell supernatants containing infectious HCV were collected for infectivity titer determination. Note that a simultaneous experiment using HUH-7 to produce HIV-1 with the identical lot of PiB did produce HIV-1 with enhanced infectivity, verifying the activity of the aliquot of PiB used to treat HCV.

Example 12

Figure 7:
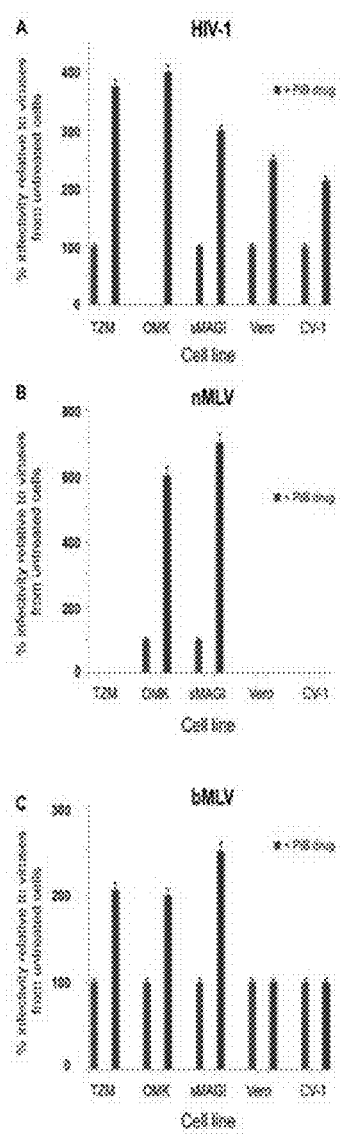

Pin1 Blocking in Producer Cell Enhances Viral Infectivity in Various Target Cells We further examined whether blocking Pin1 in producer cells can enhance the infectivity of retroviruses in different primate target cells. Viruses were produced from proviral constructs encoding HIV-1-GFP, nMLV-GFP, or bMLV-GFP with pCMV-VSV-G in the presence or absence of PiB (blue), normalized via RT assay and used to infect human TZM cells, Owl Monkey (OMK) cells, macaque sMAGI cells, and two African green monkey cell lines (Vero and CV-1). Infectivity was analyzed by GFP fluorescence via FACS. Results from the study are shown in FIG. 7. The y-axis shows percentage infectivity relative to untreated virus (set at 100%). If more cells are infected than the number infected by viruses from untreated cells, this is expressed as a value above 100%—e.g. 2000 cells/10,000 vs 4000 cells/10,000 would be 100% and 200% respectively. In FIG. 7A, identical aliquots (the same volume of the same viral supernatant from the same tube) of HIV-GFP were used to simultaneously infect the primate cell panel. Note that in the case of OMK, we obtained no infection with control HIV-1, and so infectivity is set to zero instead of 100%. Because of this, technically the boost in infectivity with PiB would be infinite. To provide an interpretable scale, the 400% boost shown is relative to the control HIV-1 infectivity seen in sMAGI cells. In FIG. 7B, identical aliquots of nMLV were used to simultaneously infect the primate cells panel. In FIG. 7C, identical aliquots of bMLV-GFP were used to simultaneously infect the primate cells panel. Each data point represents the sum of quadruplicates and the combination of three independent experiments. As shown in the figures, viruses produced in cells with Pin1 blocking have enhanced infectivity in human and nonhuman primate target cells.

Example 13

Enhanced Viral Infectivity by Blocking Pin1 in Non-human Producer Cells

Figure 8:
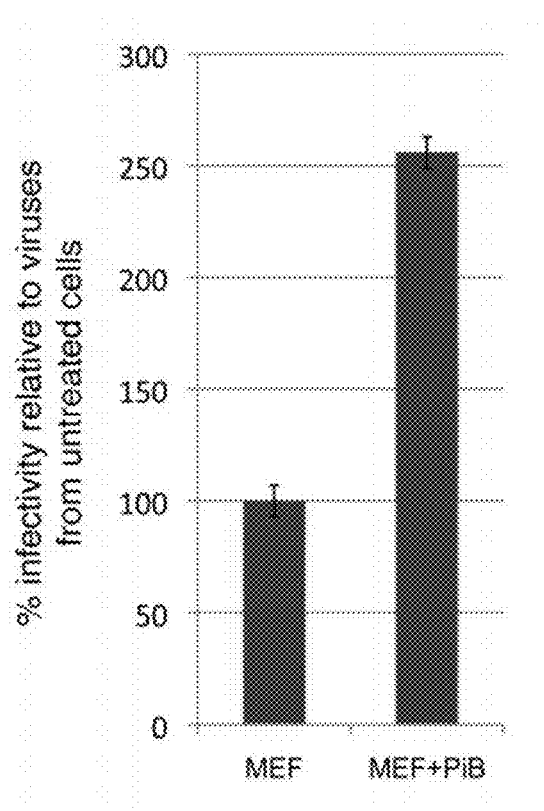

In addition to human producer cells, we also examined effect of blocked Pin activity on infectivity of viruses produced in mouse cell lines and nonhuman primate cell lines. Specifically, Murine Leukemia Virus carrying a GFP reporter was produced by co-transfecting mouse embryonic fibroblasts (MEF) with the bMLV proviral construct pCIG3-B, the reporter gene pCNCG and pCMV-VSV-G in the presence or absence of PiB. Resultant viruses were harvested and normalized via RT assay and used to infect TZM cells. Infectivity was analyzed by GFP fluorescence via FACS. The y-axis shows percentage infectivity relative to untreated virus (set at 100%). Each data point represents the sum of quadruplicates and the combination of three independent experiments. As shown in FIG. 8, MLV produced in mouse producer cells has enhanced infectivity.

Figure 9:
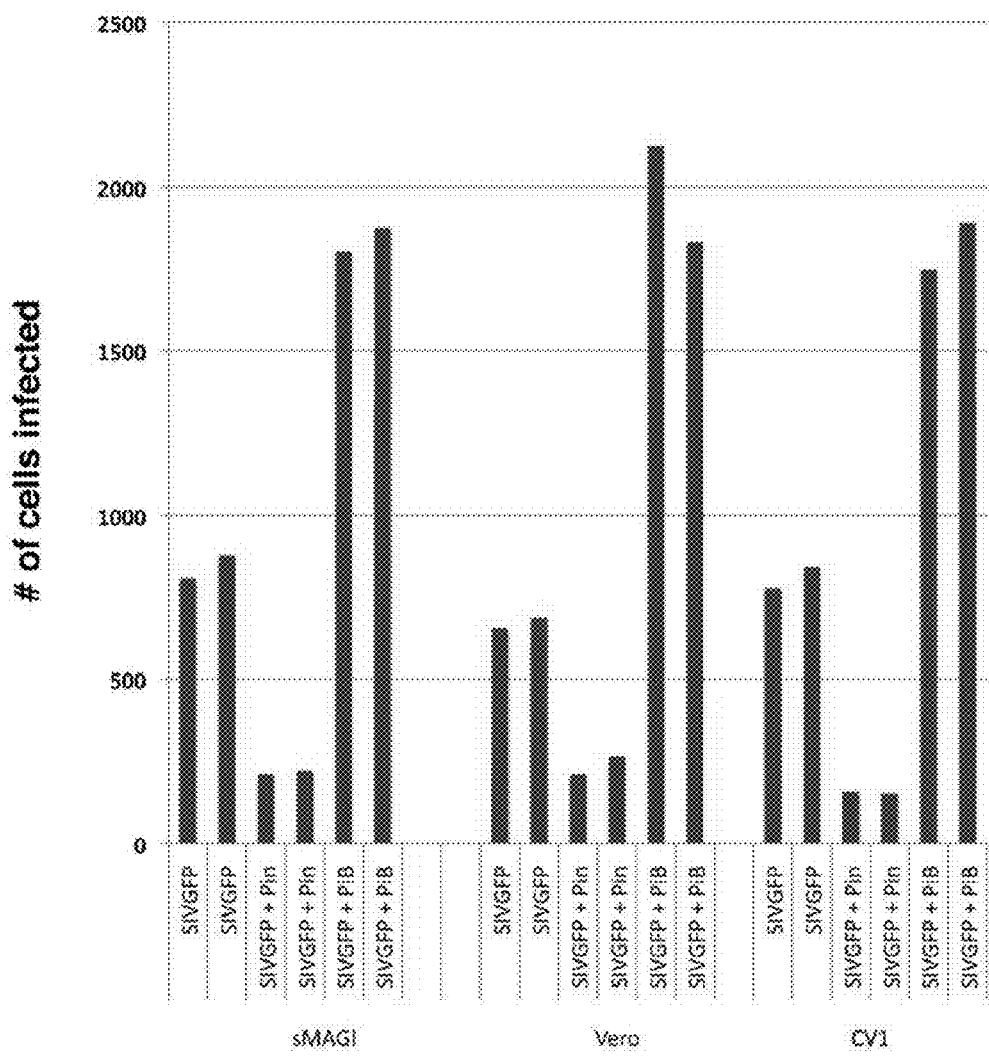

We then examined effect of Pin blocking in non-human primate producer cells on viral infectivity. Simian Immunodeficiency Viruses carrying a GFP reporter was produced by co-transfecting primate macaque sMAGI cells, and two African green monkey cell lines (Vero and CV-1) with a proviral construct encoding SIV-1-GFP (Mac293) with pCMV-VSV-G in the presence or absence of PiB. Resultant viruses were harvested and normalized via RT assay and used to infect 40,000 human TZM cells in 24 well plates. Infectivity was analyzed by GFP fluorescence via FACS. Note SIV (Mac239) does not efficiently infect TZMs at low titer. Despite this, we observe that SIV produces from cells with blocked Pin1 activity do infect human TZM cells. The results are shown in FIG. 9. As observed with human producer cells, blocking Pin1 activity in non-human primate cell lines produces viruses with enhanced infectivity.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

What is claimed is:

1. A method for producing a retrovirus with enhanced infectivity, comprising (a) transfecting a retroviral vector into a packaging cell that has suppressed expression or inhibited enzymatic activity of a parvulin prolyl peptidyl isomerase (parvulin PPIase), (b) culturing the transfected packaging cell to allow production of viral particles, thereby producing a retrovirus with enhanced infectivity.

2. The method of claim 1, further comprising harvesting viral particles from supernatant of the cultured cell.

3. The method of claim 1, wherein the packaging cell is a human cell or a monkey cell, and the parvulin PPIase is Pin1.

4. The method of claim 1, wherein the packaging cell is transfected with the vector in the presence of a compound that specifically suppresses expression or inhibits enzymatic activity of the parvulin PPIase.

5. The method of claim 1, wherein the packaging cell has suppressed expression of the parvulin PPIase.

6. The method of claim 5, wherein a gene encoding the parvulin PPIase in the packaging cell is knocked out.

7. The method of claim 5, wherein the packaging cell is treated with an inhibitory nucleic acid targeting a gene encoding the parvulin PPIase.

8. The method of claim 7, wherein the inhibitory nucleic acid is a shRNA or a siRNA.

9. The method of claim 1, wherein the packaging cell has inhibited enzymatic activity of the parvulin PPIase.

10. The method of claim 9, wherein the inhibited enzymatic activity is caused by a mutation in a gene encoding the parvulin PPIase.

11. The method of claim 9, wherein the inhibited enzymatic activity is caused by an organic antagonist compound or a peptide inhibitor.

12. The method of claim 11, wherein the antagonist compound is PiB or Juglone.

13. A method for enhancing efficiency of gene transfer with a recombinant retrovirus, comprising (a) constructing a recombinant retroviral vector expressing a target gene, (b) transfecting into a packaging cell that has suppressed expression or inhibited enzymatic activity of a parvulin prolyl peptidyl isomerase (parvulin PPIase), (c) culturing the transfected packaging cell to allow production of recombinant retroviral particles, (d) harvesting recombinant retroviral particles from supernatant of the cultured cell, and (d) transducing the recombinant retroviral particles into a target cell.

14. The method of claim 13, wherein the packaging cell is a human cell or a monkey cell, and the parvulin PPIase is Pin1.

15. The method of claim 13, wherein the packaging cell is transfected with the vector in the presence of a compound that specifically suppresses expression or inhibits enzymatic activity of the parvulin PPIase.

16. The method of claim 13, wherein the packaging cell has suppressed expression of the parvulin PPIase.

17. The method of claim 16, wherein a gene encoding the parvulin PPIase in the packaging cell is knocked out.

18. The method of claim 16, wherein the packaging cell is treated with an inhibitory nucleic acid targeting a gene encoding the parvulin PPIase.

19. The method of claim 18, wherein the inhibitory nucleic acid is a shRNA or a siRNA.

20. The method of claim 13, wherein the packaging cell has inhibited enzymatic activity of the parvulin PPIase.

21. The method of claim 20, wherein the inhibited enzymatic activity is caused by a mutation in a gene encoding the parvulin PPIase.

22. The method of claim 20, wherein the inhibited enzymatic activity is caused by an organic antagonist compound or a peptide inhibitor.

23. The method of claim 22, wherein the antagonist compound is PiB or Juglone.

24. A kit for producing a retrovirus with enhanced infectivity, comprising an inhibitor compound of a parvulin prolyl peptidyl isomerase (parvulin PPIase) and a cell line for producing the retrovirus.

25. The kit of claim 24, further comprising an instruction for culturing the cell line transfected with the retrovirus in the presence of the inhibiting compound.

26. The kit of claim 24, wherein the inhibitor compound suppresses expression of the parvulin PPIase or inhibits its enzymatic activity.

27. The kit of claim 24, wherein expression of the parvulin PPIase in the cell line has been knocked-out or knocked-down.

* * * * *